US011916156B2

(12) United States Patent
Fan et al.

(10) Patent No.: US 11,916,156 B2
(45) Date of Patent: Feb. 27, 2024

(54) METHOD AND SYSTEM FOR OPTICAL DETECTION USING A BIOMIMETIC ELECTROCHEMICAL EYE

(71) Applicant: The Hong Kong University of Science and Technology, Hong Kong (CN)

(72) Inventors: Zhiyong Fan, Hong Kong (CN); Leilei Gu, Hong Kong (CN)

(73) Assignee: THE HONG KONG UNIVERSITY OF SCIENCE AND TECHNOLOGY, Hong Kong (CN)

(*) Notice: Subject to any disclaimer, the term of this patent is extended or adjusted under 35 U.S.C. 154(b) by 422 days.

(21) Appl. No.: 17/225,791

(22) Filed: Apr. 8, 2021

(65) Prior Publication Data

US 2021/0315685 A1  Oct. 14, 2021

Related U.S. Application Data

(60) Provisional application No. 63/100,942, filed on Apr. 9, 2020.

(51) Int. Cl.
*H01L 31/0352* (2006.01)
*A61F 2/14* (2006.01)
(Continued)

(52) U.S. Cl.
CPC ...... *H01L 31/035227* (2013.01); *A61F 2/141* (2013.01); *B25J 19/021* (2013.01);
(Continued)

(58) Field of Classification Search
CPC ............ H01L 31/035227; A61F 2/141; A61F 2210/0076; A61F 2230/0071;
(Continued)

(56) References Cited

U.S. PATENT DOCUMENTS 6,201,574 B1  3/2001 Martin
7,742,090 B2  6/2010 Street et al.
(Continued)

FOREIGN PATENT DOCUMENTS

CN  106618598 A  5/2017

OTHER PUBLICATIONS

Choi, Changsoon, et al., "Human eye-inspired soft optoelectronic device using high-density MoS$_2$-graphen curved image sensor array", *Nature Communications*, 8:1664, pp. 1-11, (Nov. 21, 2017).
(Continued)

*Primary Examiner* — Que Tan Le
*Assistant Examiner* — Mai Thi Ngoc Tran
(74) *Attorney, Agent, or Firm* — Leydig, Voit & Mayer, Ltd.

(57) ABSTRACT

A system comprising a biomimetic electrochemical eye (EC-EYE) and a computing device is provided. The EC-EYE comprises: an ionic liquid device; a nanowire (NW) device that comprises the plurality of NWs; and a connection device configured to provide a plurality of currents associated with the plurality of NWs to a computing device. The computing device comprises one or more processors and a display device. The one or more processors are configured to: receive the plurality of currents from the plurality of NWs via the connection device; determine a plurality of pixel characteristics associated with a plurality of pixels based on the plurality of currents from the plurality of NWs; generate an image comprising the plurality of pixels based on the plurality of pixel characteristics; and provide the image to a display device. The display device is configured to display the image.

20 Claims, 23 Drawing Sheets

(51) Int. Cl.
G06T 3/00 (2006.01)
B25J 19/02 (2006.01)
G09B 23/30 (2006.01)
B33Y 80/00 (2015.01)
H04N 5/262 (2006.01)

(52) U.S. Cl.
CPC ............ *B33Y 80/00* (2014.12); *G06T 3/0018* (2013.01); *G09B 23/30* (2013.01); *H04N 5/2628* (2013.01); *A61F 2210/0076* (2013.01); *A61F 2230/0071* (2013.01); *A61F 2250/0024* (2013.01); *A61F 2250/0028* (2013.01); *A61F 2250/0043* (2013.01)

(58) Field of Classification Search
CPC ...... A61F 2250/0024; A61F 2250/0028; A61F 2250/0043; A61F 2/14; B25J 19/021; B33Y 80/00; G06T 3/0018; G09B 23/30; H04N 5/2628; G01N 27/26; G01N 21/17; G01N 2021/1765; B32B 1/00; B32B 3/085; B32B 3/266; B32B 15/017; B32B 15/08; B32B 15/20; B32B 27/283
USPC ....................................................... 250/208.1
See application file for complete search history.

(56) References Cited

U.S. PATENT DOCUMENTS

| | | | |
|---|---|---|---|
| 7,904,163 | B2 | 3/2011 | Greenberg et al. |
| 8,322,027 | B1 | 12/2012 | Greenberg et al. |
| 9,099,603 | B2 | 8/2015 | Roy et al. |
| 10,799,132 | B2 | 10/2020 | Negi et al. |
| 2016/0256677 | A1 | 9/2016 | Song et al. |
| 2016/0286102 | A1 | 9/2016 | Sulfridge et al. |
| 2019/0386044 | A1 | 12/2019 | Lee et al. |
| 2021/0192978 | A1* | 6/2021 | Liu .......................... G09B 23/32 |

OTHER PUBLICATIONS

Pang, Yantao, et al., "Cylindrical and Spherical Membranes of Anodic Aluminum Oxide with Highly Ordered Conical Nanohole Arrays", *Nature Science*, vol. 7, pp. 232-237, (May 2015).
Asuo, Ivy M., et al. "Highly Efficient and Ultrasensitive Large-Area Flexible Photodetector Based on Perovskite Nanowires", *Small*, vol. 15, 1804150. 7 pages, (2019).
Guenter, Brian, et al., "Highly curved image sensors: a practical approach for improved optical performance", *Optics Express*, vol. 25, No. 12, (Jun. 12, 2017).
Gu, L., et al., 3D Arrays of 1024-Pixel Image Sensors based on Lead Halide Perovskite Nanowires, *Advance Materials*, 28, pp. 9713-9721 (2016).
Jung, I, et al., Dynamically tunable hemispherical electronic eye camera system with adjustable zoom capability, *Proc Natl. Acad. Sci.*, vol. 108, No. 5, pp. 1788-1793, (Feb. 1, 2011).
Nassi, J.J., et al., Parallel Processing Strategies of the Primate Visual System, *Nat. Rev. Neurosci*, 10(5), pp. 360-372, (May 2009).
Dickey, M.D., et al., "Eutectic Gallium-Indium (EGaIn): A Liquid Metal Alloy for the Formation of Stable Structures in Microchannels at Room Temperature", *Advanced Functional Materials*, 18, 33. 1097-1104, (Apr. 18, 2008).
Zhang, K., et al., "Origami silicon optoelectronics for hemispherical electronic eye system", *Nature Communications*, 8, pp. 1-8, (Nov. 24, 2017).
Han, Q., et al., Single Crystal Formamidinium Lead lIodide (FAPbI$_3$): Insight into Structural, Optical and Electrical Properties:, *Advance Materials*, 28(11), pp. 2253-2258, (2016).
Fan, Z., et al., "Three-dimensional nanopillar-array photovoltaics on low-cost and flexible substrates", *Nature, Materials*, 8, pp. 648-653, (2009).

Wen, C.Y., et al., "Formation of Compositionally Abrupt Axial Heterojunctions in Silicon-Germanium Nanowires", *Science*, vol. 326, pp. 1247-1250, (Nov. 27, 2009).
Kawano, R., et al., "Equilibrium Potentials and Charge Transport of an I$^-$/I$_3^-$Redox Couple in an Ionic Liquid", *Chem, Commun.*, 3, 33, pp. 330-331, (Feb. 2003).
Rayner, K., et al., "Eye Movements and Visual Encoding During Scene Perception", *Psychol. Sci.*, 20, pp. 6-10, (Jan. 2009).
Mustafi, D., et al., "Structure of Cone Photoreceptors", *Prog. Retin. Eye Res.* 28(4), pp. 289-302, (Jul. 2009).
Ayton, L.N., et al. "First-in-Human Trial of a Novel Suprachoroidal Retinal Prosthesis", *PLoS/One*, 9(12), pp. 1-26, (Dec. 2014).
Shivdasani, M.N., et al. "Factors Affecting Perceptual Thresholds in a Suprachorodial Retinal Prosthesis", *Investigation Ophthalmology & Visual Science*, 55, pp. 6467-6481, (Oct. 2014).
Navarro, R., "The Optical Design of the Human Eye: a Critical Review", *J. Optom.* vol. 2, pp. 3-18, (Jan.-Mar. 2009).
Xie, Y., et al. "A self-powered UV photodetector based on TiO$_2$ nanorod arrays", *Nanoscale Research Letters.*, 8,188, pp. 1-6, (2013).
Lin, H., et al., "High-Performance Self-powered Photodetectors Based on ZnO/ZnS Core-Shell Nanorod Arrays", *Nanoscale Research Letters*, 11, Article No. 420 (2016).
Zeng, Y., "The enhancement of a self-powered UV photodetector based on vertically aligned Ag-modified ZnO nanowires", *RSC Adv.*, 5., p. 66738-66741, (2015).
Ren, X, et al., "Environmentally Robust Black Phosphorus Nanosheets in Solution: Application for Self-Powered Photodectector", *Advanced Functional Materials*, 27, 1606834, pp. 1 of 8, (2017).
Li, Jieni, et al., "A high-performance ZnO based photoelectrochemical cell type UV photodetector with [Co(bpy)$_3$]$^{3+/2+}$electrolyte and PEDOT/ITO counter electrode", *RSC Advances*, 7, pp. 18987-18992, (2017).
Lin, P., et al., "A tunable ZnO/electrolyte heterojunction for a self-powered photodetector", *Phys. Chem. Chem. Phys.* 16, p. 26697-26700, (2014).
Patel, D.B., et al., "Unraveling the photoelectrochemical properties of ionic liquids: cognizance of partially reversible redox activity", *Phys. Chem. Chem. Phys.* 16, p. 22735-22744, (2014).
Li, X., et al., "High-Performance Photoelectrochemical-Type Self-Powered UV Photodetector Using Epitaxial TiO$_2$/SnO$_2$ Branched Heterojunction Nanostructure", *Small*, 9, pp. 2005-2011, (2013).
Hou, Xiao Juan, et al., "SnO$_2$@TiO$_2$ Heterojunction Nanostructures for Lithium-Ion Batteries and Self-Powered UV Photodetectors with Improved Performance", *Chem Electro Chem*, 1(1), pp. 108-115 (Jan. 3, 2014).
Yu, Xiaoyun, "Self-assembled 2D WSe$_2$ thin films for photoelectrochemical hydrogen Production", *Nature Communications*, 6, 7596, (2015).
Gu, L., et al., "Significantly improved black phase stability of FAPbI$_3$ nanowires via spatially confined vapor phase growth in nanoporous templates", *Nanoscale*, 10, pp. 15164-15172, (2018).
Waleed, A., et al., "Lead-Free Perovskite Nanowires Array Photodetectors with Drastically Improved Stability in Nanoengineering Templates", *Nano Letters*, 17:(1), pp. 523-530, (2017).
Song, Y.M., et al., "Digital cameras with designs inspired by the arthropod eye", *Nature* 497, pp. 95-99, (May 2, 2013).
Fan, Z., et al., "Ordered Arrays of Dual-Diameter Nanopillars for Maximized Optical Absorption", *Nano Lett.*, 10(10), pp. 3823-3827, (2010).
Jonas, J.B., et al., Abstract, "Count and Density of Human Retinal Photoreceptors", *Graefes Arch. Clin. Exp. Ophthalmol*, 230, (6):505-10, (1992).
Pocock, D.C.D., Sight and Knowledge, *Transactions Institute British Geographers*, vol. 16, No. 4, pp. 385-393, (1981).
Ko, Heung Cho, et al., "A hemispherical electronic eye camera based on compressible silicon optoelectronics", *Nature* 454, pp. 748-753, (2008).
Ramdani, M.R., et al., "Fast Growth Synthesis of GaAs Nanowires with Exceptional Length", *Nano Letters*, 10, pp. 1836-1841, (2010).
Wandell, B.A., "Foundations of Vision" presented at *Photonics Spectra Conference 2021*, Color research and application, vol. 21, No. 2, pp. 142-144, (Apr. 1996).

(56) References Cited

OTHER PUBLICATIONS

Boschloo, G., et al., "Characteristics of Iodide/Triiodide Redox Mediator in Dye-Sensitized Solar Cells", *Accounts of Chemical Research*, 42:(11), pp. 1819-1826, (Nov. 2009).

Fujikado, T., et al., "Evaluation of phosphenes elicited by extraocular simulation in normals and by suprachoroidal-trans retinal simulation in patients with retinitis pigmentosa", *Graefe's Archive for Clinical and Experimental Ophthalmology*, 245, pp. 1411-1419, (Mar. 2007).

Kim, C.W., et al., "Fabrication of $SrTiO_{3-TiO2}$ heterojunction photonanode with enlarged pore diameter for dye-sensitized solar cells", *Journal of Materials Chemistry A*, RSC Publishing, pp. 11820-11827, (2013).

Li, Z., et al., "High-Performance Photo-Electrochemical Photodetector Based on Liquid-Exfoliated Few-Layered InSe Nanosheets with Enhanced Stability", *Advanced Functional Materials*, 28, 1705237, pp. 1-7, (Dec. 2018).

Wang, Z., et al., "Multilayer $TiO_2$nanorod cloth/nanorod array electrode for dye-sensitized solar cells and self-Powered UV detectors", *Nanoscale* 4, pp. 3350-3358, (2012).

Waleed, A., et al., "All Inorganic Cesium Lead Iodide Pervskite Nanowires with Stabilized Cubic Phase as Room Temperature and Nanowire Array-Based Photodetectors", *Nano Letters*, 17, pp. 4951-4957, (2017).

Zhang, et al., "Increasing Photoluminescence Quantum Yield by Nanophotonic Design of Quantum-Confined Halide Perovskite Nanowire Arrays" *Nano Letters*, 19, pp. 2850-2857, (2019).

Gu, L., et al., "A biomimetic eye with a hemispherical perovskite nanowire array retina", *Nature*, vol. 581, pp. 278-284, (May 21, 2020).

Kim, Min Sung, et al., An aquatic-vision-inspired camera based on a monocentric lens and silicon nanorod photodiode array, *Nature Electronics*, 3(9), pp. 546-553, (2020).

Schein, S.J., "Anatomy of Macaque Fovea and Spatial densities of Neurons in Foveal Representation", *The Journal of Comparative Neurology*, 269, 99, pp. 479-505, (1988).

Atchison, D.A., et al., "Optics of the human eye", (vol. 35), *Oxford: Butterworth-Heinemann*, (2000), citing "The retina" on pp. 5-7, Table 1.1 on p. 6, and the "Field of vision" on p. 8 and "Purpose of the pupillary light response" on p. 27.

\* cited by examiner

METHOD AND SYSTEM FOR OPTICAL DETECTION USING A BIOMIMETIC ELECTROCHEMICAL EYE

CROSS-REFERENCE TO RELATED APPLICATIONS

This patent application claims the benefit of U.S. Provisional Patent Application No. 63/100,942, filed Apr. 9, 2020, which is incorporated by reference herein.

BACKGROUND

Biological eyes are arguably the most important sensing organ for most of the animals on this planet. In fact, the human brain acquires more than eighty percent of information about their surroundings using the eyes. A human eye, with a concavely hemispherical retina and light-management components, is particularly notable for its exceptional characteristics including a wide field of view (FOV) of up to 150°, high resolution of 1 arcminute (arcmin) per line pair at the fovea, and excellent adaptively to the optical environment. In particular, the dome shape of the retina has the merit of reducing the complexity of optical systems by directly compensating for the aberration from the curved focal plane.

Mimicking human eyes, artificial vision systems play the same important role in autonomous technologies such as robotics. However, the commercial charge-coupled device (CCD) and complementary-metal-oxide-semiconductor (CMOS) image sensors that are currently used within the artificial vision systems are dominantly using planar device structures shaped by mainstream planar microfabrication processes, which makes it difficult for hemispherical device fabrication. In other words, the majority of image sensors that are currently being manufactured and used by artificial vision systems are planar (e.g., 2-dimensional) rather than hemispherical (e.g., 3-dimensional and shaped like a human's eye). By not being hemispherical, these sensors do not share the many exceptional device characteristics and above advantages of being shaped like a human's eye. Furthermore, particularly for humanoid robots, the vision system seeks to be designed to resemble that of a human's eyes in appearance as much as possible to enable amicable human-robot interaction. Accordingly, there remains a technical need for a hemispherical image sensor design mimicking that of human retina.

SUMMARY

In an exemplary embodiment, the present application provides a system comprising a biomimetic electrochemical eye (EC-EYE) and a computing device. The EC-EYE comprises: an ionic liquid device comprising ionic liquid that serves as an electrolyte to a plurality of nanowires (NWs); a nanowire (NW) device that comprises the plurality of NWs configured to generate a plurality of currents based on a detected light intensity; and a connection device operatively coupled to the NW device, wherein the connection device is configured to provide the plurality of currents associated with the plurality of NWs to a computing device. The computing device comprises one or more processors and a display device. The one or more processors are configured to: receive the plurality of currents from the plurality of NWs via the connection device; determine a plurality of pixel characteristics associated with a plurality of pixels based on the plurality of currents from the plurality of NWs; generate an image comprising the plurality of pixels based on the plurality of pixel characteristics; and provide the image to a display device. The display device is configured to display the image.

In some instances, the connection device comprises a plurality of connector. The one or more processors are configured to determine the plurality of pixel characteristics by: determining a pixel characteristic for each pixel of the plurality of pixels based on currents generated by a subset of NWs of the plurality of NWs, wherein each of the subset of NWs is associated with a connector, of the plurality of connectors, that connects the subset of NWs to the computing device and is assigned to a single pixel from the plurality of pixels, and wherein the currents from the subset of NWs are used to determine the pixel characteristic for that single pixel.

In some examples, the pixel characteristic is a luminance value or a red, green, blue (RGB) value. The one or more processors are configured to determine the pixel characteristic for each pixel by: determining the luminance value or the RGB value based on a value of the currents generated by the corresponding subset of NWs, wherein the value of the currents is based on the detected light intensity.

In some variations, the one or more processors are configured to determine the pixel characteristic for each pixel based on a summation of the currents generated by the subset of NWs that are assigned to the pixel.

In some instances, the EC-EYE further comprises: a tungsten film contact configured to operate as a counter electrode to the plurality of NWs.

In some examples, the connection device comprises a plurality of liquid metal (LM) nerve fibers, wherein each of the connectors is an LM nerve fiber from the plurality of LM nerve fibers.

In some variations, the EC-EYE further comprises: a polydimethylsiloxane (PDMS) eye socket configured to integrate and align the plurality of LM nerve fibers with the plurality of NWs; and an indium adhesion layer configured to be an electrical contact between the plurality of NWs and the plurality of LM nerve fibers, wherein the NW device is a NW array retina that is hemispherical in shape and the EC-EYE is spherical in shape.

In some instances, the system further comprises: a multiplexer, wherein each of the plurality of LM nerve fibers is an input to the multiplexer and an output of the multiplexer is provided to the computing device, wherein each of the inputs of the multiplexer is associated with a pixel from the plurality of pixels.

In some examples, the NW device is a hemispherical porous-alumina-membrane (PAM) and the plurality of NWs are grown inside the hemispherical PAM using a vapor-phase process.

In some variations, the plurality of NWs comprise a metal-halide perovskite material, a silicon (Si) material, a germanium (Ge) material, an indium phosphide (InP) material, or a gallium arsenide (GaAs) material.

In some instances, the NW device is a planar porous-alumina-membrane (PAM), wherein the connection device is a Copper (Cu) electrode that is operatively coupled to the plurality of NWs, and wherein the Cu electrode is configured to provide the plurality of currents generated by the plurality of NWs to the computing device.

In some examples, the planar PAM is fabricated using a two-step anodization process followed by mercury (II) chloride ($HgCl_2$) etching, wherein the plurality of NWs are a plurality of perovskite NWs, and wherein the plurality of perovskite NWs are grown within a plurality of channels within the planar PAM.

In some variations, the connection device comprises a plurality of microneedles that are configured to provide the plurality of currents generated by the plurality of NWs to the computing device, wherein each microneedle is associated with a subset of NWs of the plurality of NWs and configured to provide only the current generated from the subset of NWs to the computing device.

In some instances, the plurality of microneedles are a plurality of nickel (Ni) microneedles, wherein each subset of NWs comprises three NWs, and wherein each microneedle is configured to provide the current generated by the three corresponding NWs to the computing device.

In some examples, the system further comprises: a multiplexer, wherein each of the plurality of microneedles is an input to the multiplexer and an output of the multiplexer is provided to the computing device, wherein the one or more processors are configured to determine the plurality of pixel characteristics based on: determining a pixel characteristic, from the plurality of pixel characteristics, of a pixel based on a received current of the plurality of currents; determining a corresponding input of the multiplexer that provided the received current; and determining a location of the pixel within the image based on the corresponding input of the multiplexer.

In another exemplary embodiment, the present application provides a method, comprising: receiving, by a computing device, a plurality of currents from a plurality of nanowires (NWs) of a biomimetic electrochemical eye (EC-EYE), wherein the EC-EYE comprises the plurality of NWs, an ionic liquid device, and a connection device, wherein the ionic liquid device comprises ionic liquid that serves as an electrolyte to the plurality of NWs, wherein the plurality of NWs are configured to generate a plurality of currents based on a detected light intensity, and wherein the connection device is operatively coupled to the NW device and configured to provide the plurality of currents associated with the plurality of NWs to the computing device; determining, by the computing device, a plurality of pixel characteristics associated with a plurality of pixels based on the plurality of currents from the NWs; generating, by the computing device, an image comprising the plurality of pixels based on the plurality of pixel characteristics; and causing, by the computing device, display of the image on a display device.

In some instances, the connection device comprises a plurality of connectors, and wherein determining the plurality of pixel characteristics comprises: determining a pixel characteristic for each pixel of the plurality of pixels based on currents generated by a subset of NWs of the plurality of NWs, wherein each subset of NWs is associated with a connector, of the plurality of connectors, that connects the subset of NWs to the computing device and is assigned to a single pixel from the plurality of pixels, and wherein the currents from the subset of NWs are used to determine the pixel characteristic for that single pixel.

In some examples, the pixel characteristic is a luminance value or a red, green, blue (RGB) value, and wherein determining the pixel characteristic for each pixel comprises: determining the luminance value or the RGB value based on a value of the current generated by the corresponding subset of NWs, wherein the value of the current is based on the detected light intensity.

In yet another exemplary embodiment, the present application provides a biomimetic electrochemical eye (EC-EYE), comprising: a nanowire (NW) device that comprises a plurality of perovskite NWs, wherein each of the plurality of perovskite NWs is configured to generate a current based on a detected light intensity, and wherein the plurality of perovskite NWs are grown on the NW device using a vapor-phase process, wherein the NW device is hemispherical and the EC-EYE is spherical; a plurality of liquid metal (LM) nerve fibers operatively coupled to the NW device, wherein the plurality of LM nerve fibers are configured to provide a plurality of currents associated with the plurality of perovskite NWs to a computing device, wherein each of the LM nerve fibers is electrically connected to a subset of the plurality of perovskite NWs; and a polydimethylsiloxane (PDMS) eye socket with a hole array for the plurality of LM nerve fibers, wherein the PDMS nerve socket is fabricated using a 3-dimensional (3-D) printer, wherein the plurality of LM nerve fibers are injected into tubes using LM patterning and inserted into holes of the hole array.

In some instances, the NW device is a hemispherical porous-alumina-membrane (PAM), and wherein the EC-EYE further comprises: an indium adhesion layer that is operatively coupled to the hemispherical PAM, wherein the indium adhesion layer is evaporated onto a side of the PAM opposite the plurality of perovskite NWs; a hemispherical aluminum (Al) shell that is coated with a tungsten film and configured to be a counter electrode for the EC-EYE; and an ionic liquid humour that comprises an ionic liquid and positioned between the AL shell that is coated with the tungsten film and the PAM.

DETAILED DESCRIPTION

Exemplary embodiments of the present application provide an artificial visual system that comprises a biomimetic electrochemical eye (EC-EYE) with hemispherical retina made of a high-density semiconducting nanowire (NW) array and a method for using the artificial visual system. Further exemplary embodiments of the present application provide systems and methods of growing or manufacturing the EC-EYE using a vapor-phase approach. For example, the semiconducting NW array may be manufacturing using any material with a photoelectric effect, such as, but not limited to, metal-halide perovskites, Silicon (Si), Germanium (Ge), Indium Phosphide (InP), Gallium Arsenide (GaAs), and/or other suitable materials, components, or elements. Below, the EC-EYE will be described as being manufactured using metal-halide perovskite in order to describe the device structure and working mechanism. However, in other examples, the EC-EYE may be made of Si, Ge, and/or another material with a photoelectric effect. In the EC-EYE, the ionic liquid electrolyte may be used as a front side common contact to the NWs and liquid metal (LM) wires may be used as back contacts to NW photo sensors, which may mimic human nerve fibers behind the retina. Device characterizations and advantages may manifest such as the EC-EYE may have a high responsivity, reasonable response speed, low detection limit as well as wide field of view (FOV). In other words, due to the shape (e.g., the hemispherical shape) and/or design of the EC-EYE, the EC-EYE may have and/or acquire the advantages typically associated with a human eye. Further, the EC-EYE may also demonstrate the basic function of a human eye to acquire image patterns. In addition to structural similarity with a human eye, the hemispherical artificial retina has NW density much higher than that of photoreceptors in a human retina and thus, may potentially achieve a higher image resolution, which may bolstered by implementation of a single-NW based ultra-small photodetector.

Figure 1:
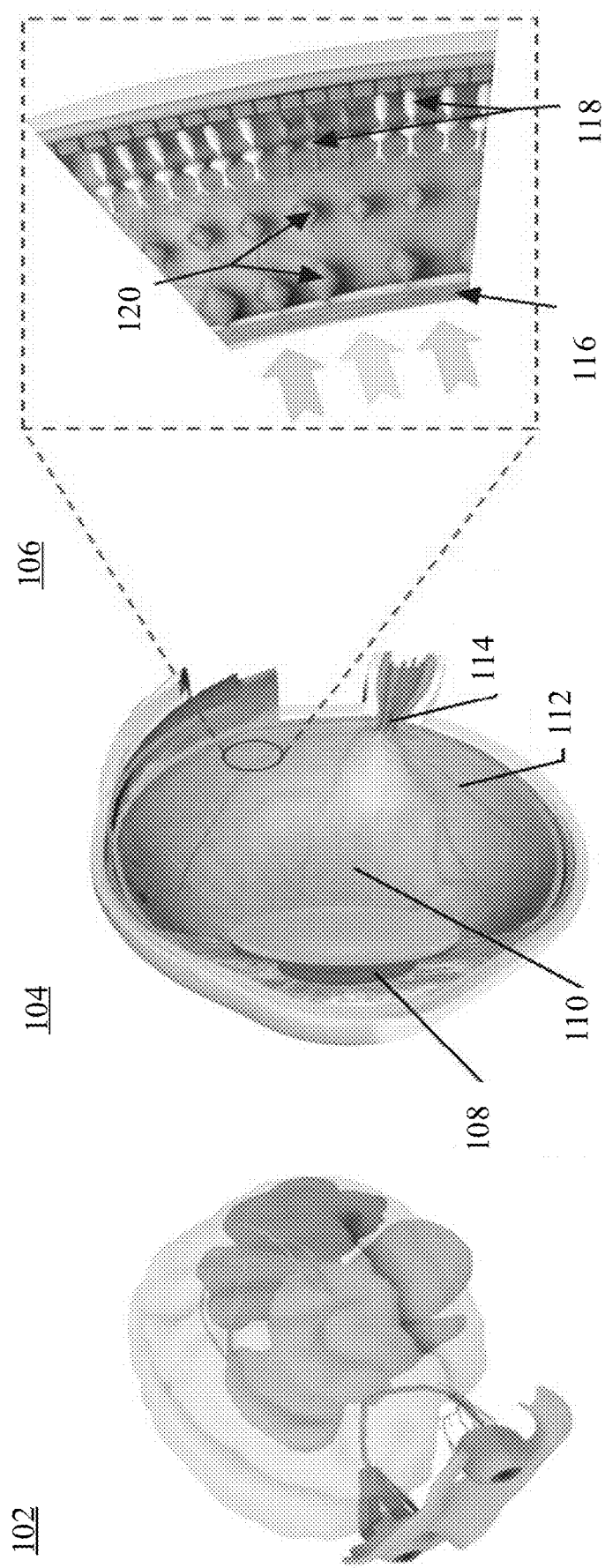
FIG. 1 shows a schematic of a human imaging system.
Figure 2:
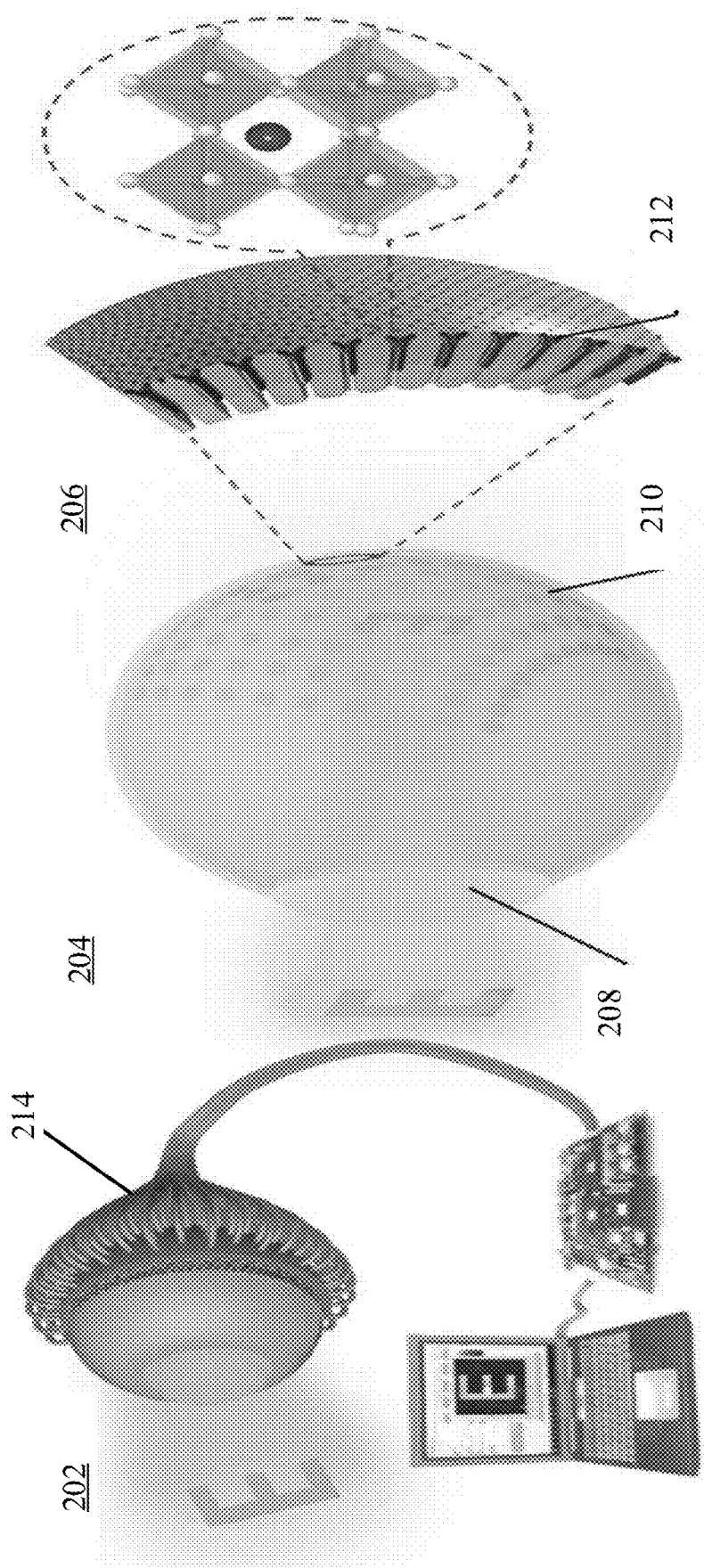
FIG. 2 shows a schematic of a spherical biomimetic electrochemical eye (EC-EYE) imaging system.

FIGS. 1 and 2 show a schematic comparison of human (FIG. 1) and EC-EYE imaging systems (FIG. 2). In particular, FIGS. 1 and 2 include three sections each and each section shows a different image. Section 102 shows the human visual system, which is a comprehensive system with two eye bulbs for optical sensing, millions of nerve fibers for data transmission, and a brain for data processing. The human brain has a spectacular capability of parallel processing. For instance, neuro-electric signals from around one million nerve fibers may be processed simultaneously and thus image processing/recognition may be implemented in a very short time. The internal structure of a human eye, which is shown in section 104, includes a lens 108, a spherical cavity, a vitreous humour 110, a hemispherical retina 112, and the nerve fibers 114. In this structure, the vitreous humour 110 is the transparent gelatinous tissue filling the eyeball behind the lens 108 and the retina 112 is the core component to convert optical images to neuro-electric signals. The hemispherical shape simplifies eye optical design, which results in extraordinarily large FOV of around 155° with a wide visual perception of the surrounding. Section 106 shows the retina of the human eye with the photoreceptors 118, neurons 120, and optic nerves 116. There are around 100-120 millions of photoreceptors 118 and/or rod and cone cells vertically assembled in the retina 112 in a dense and quasi-hexagonal manner. The density of these photo-sensing cells 118 is around 10 million per $cm^2$ with 3 μm average pitch, leading to a high imaging resolution comparable with that of the state-of-the-art CCD/CMOS sensors. However, the nerve fiber layer is at the front surface of human retina causing light loss and blind spot issues. For example, there may be light loss through the optic nerve layers 116. As the nerve fibers route in front of the retina 112, there is a "via" where the fibers pass through the retina 112. This "via" may be a blind spot on the retina 112 where there is no photoreceptor 118.

Referring to FIG. 2, section 202 shows the overall EC-EYE imaging system including the EC-EYE, section 204 shows the EC-EYE, and section 206 shows the perovskite NWs in porous-alumina-membrane (PAM) template and their crystal structure. In particular, sections 202, 204, and 206 show the schematic of the biomimetic visual system including the lens 208, the retina 210 (e.g., NW retina), the photo-sensor array 212 (e.g., a NW photoreceptor) on a hemispherical substrate, and the thin liquid metal (LM) wires (e.g., LM fibers) 214 as electrical contacts. The lens 208, the photo-sensor array 212 on a hemispherical substrate, and the thin LM wires 214 components mimic biological eye lens, retina and nerve fibers behind the retina, respectively. The artificial retina is made of a high-density array 212 of perovskite NWs. In some instances, the perovskite NWs are grown inside hemispherical porous-alumina-membrane (PAM) using a vapor-phase process. Additionally, and/or alternatively, certain components of the EC-EYE may be fabricated and/or manufactured using 3-dimensional (3-D) printing and/or liquid metal patterning. The fabrication/manufacturing process will be described below.

To put it another way, among other embodiments, the present application describes using an EC-EYE that has a spherical structure with a hemispherical image sensor to capture images as well as a process to fabricate this spherical EC-EYE using a NW array. The NW array may be manufactured from perovskite and/or other optoelectronic semiconductor materials (e.g., Si, Ge, and/or other materials described above) that emulate photoreceptors. The vapor process may be a method to grow the NWs including NWs that are made of perovskite, Si, and Ge. The NWs made from the vapor process may have better material properties than when they are made from other methods.

Figure 3A:
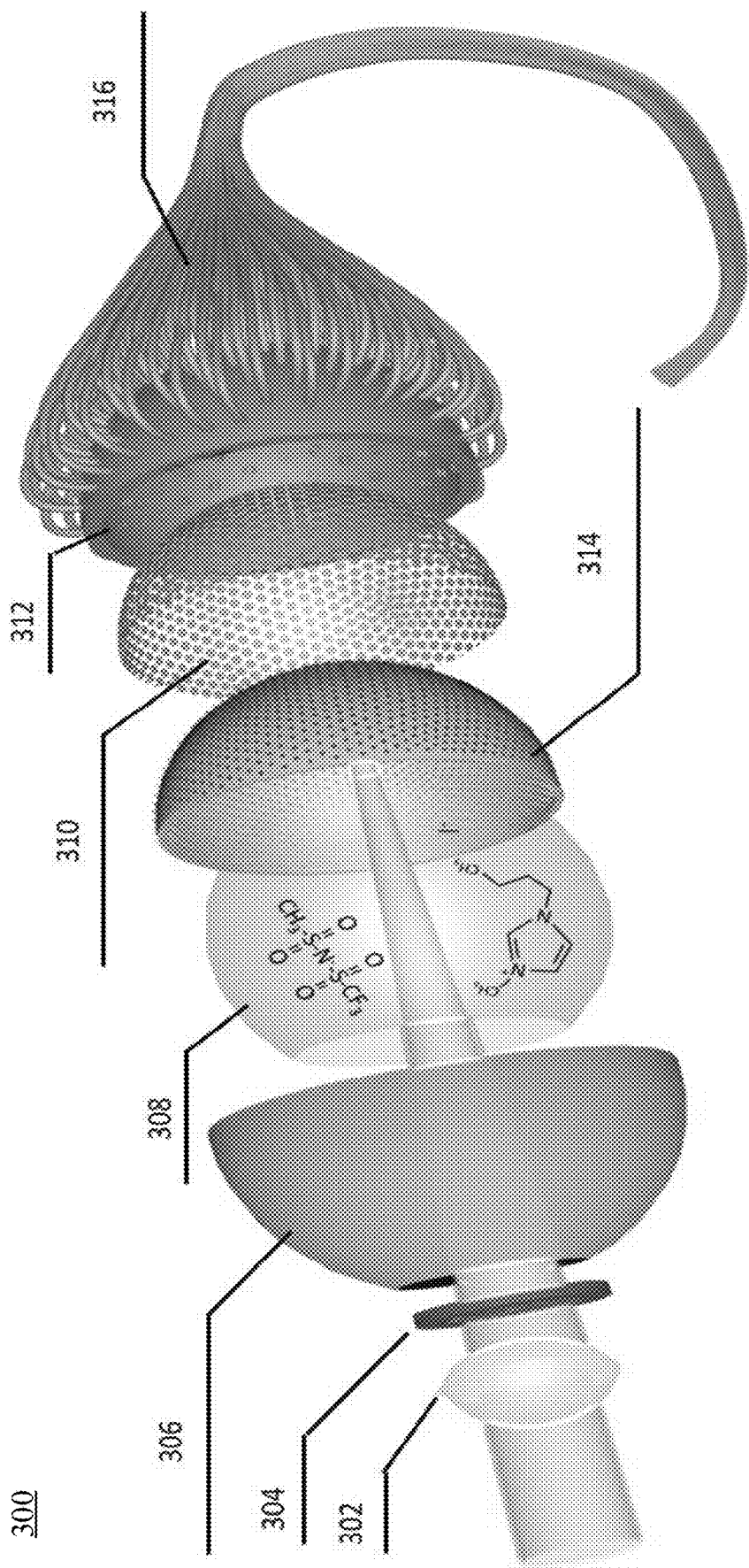
FIG. 3A shows an exploded view of an EC-EYE.

FIG. 3A shows an exploded view of the EC-EYE of FIG. 2. The EC-EYE 300 includes a lens 302, an aperture 304, an Aluminum (Al) shell sclera and Tungsten (W) film contact 306, an ionic liquid device (e.g., ionic liquid humour) 308, an indium adhesion layer 310, a Polydimethylsiloxane (PDMS) eye socket 312, an NW array device (e.g., NW array retina) 314, and liquid metal (LM) nerve fibers 316. The NWs 314 (e.g., the NW array retina) serve as light-sensitive working electrodes. The Tungsten (W) film on Aluminum (Al) hemispherical shell 306 operates as the counter electrode. In between the two electrodes (e.g., 314 and 306), ionic liquid is used to fill in the spherical cavity (e.g., the ionic liquid humour 308) serving as the electrolyte, mimicking the vitreous humour in the human eye. There is also an aperture 304 as the counterpart of a pupil in a human eye. The Indium adhesion layer 310 is an alloy with liquid metal that is used to improve the electrical contact between the NWs (e.g., the NW array retina 314) and the LM fibers 316. The PDMS eye socket 312 is used to integrate and align the LM fibers 316 to form a pixel array. The flexible LM wires 316 (e.g., Eutectic-Gallium-Indium (EGaIn) LM wires) in soft rubber tubes are used for signal transmission between NWs 314 (e.g., the NW array retina) and external circuitry (e.g., a processor, controller, and/or other type of computing device, which is described below, that may be used to process the image captured by the EC-EYE 300).

An individual photodetector includes a set of NWs from the NW array retina 314, the ionic liquid humour 308, the hemispherical shell 306 and a single LM nerve fiber 316. In operation, the individual photodetector may be addressed and measured by selecting the corresponding LM wire from the liquid metal nerve fibers 316. The photodetector may be used to determine pixel characteristics for one pixel within the image. This resembles the working principle of human retina in which groups of photoreceptors are individually connected with nerve fibers, enabling suppressed interference among pixels and high-speed parallel processing of the neuro-electric signals. In other words, the NW array retina 314 comprises (e.g., holds) a plurality of NWs that are responsible for detecting pixels of an image. For instance, a distribution of light (e.g., a particular pattern) may enter into the EC-EYE 300 and may be focused on at least some of the NWs of the NW array retina 314. For instance, a first set of NWs for a first photodetector may be illuminated, which yields a higher current, whereas a second set of NWs for a second photodetector are not illuminated and thus maintain a lower current. The NWs are electrically connected to the LM nerve fibers 316 and the LM nerve fibers 316 are electrically connected to a computing device. Each LM nerve fiber 316 may be connected to a plurality of NWs (e.g., hundreds, tens of thousands, or even half a million or greater NWs) from the NW array retina 314 and a photodetector comprises an LM nerve fiber along with their connected NWs. As mentioned above, each photodetector is responsible for one pixel within an image. For instance, computing device may receive the current from each of the photodetectors (e.g., a first photodetector that comprises a first LM nerve fiber with the first subset of NWs and a second photodetector that comprises a second LM nerve fiber with the second subset of NWs) and record the current as well as the photodetector that is associated with the current. Then, using the received/recorded current as well as the photodetector, the computing device may reconstruct an image of the pattern.

To put it another way, an image generated by a computing device may have a plurality of pixels (e.g., a simple image may have 100 total pixels with 10 pixels in each row and 10 pixels in each column). Each photodetector may be assigned to produce a single pixel within an image (e.g., a first photodetector may be assigned to produce a first pixel such as the pixel in row 1, column 1 and a second photodetector may be assigned to produce a second pixel such as the pixel in row 1, column 2). For instance, if an image has 100 total pixels, then there may be 100 total photodetectors, which may result in 100 LM nerve fibers 316 and each of the LM fibers may comprise a plurality (e.g., 1,500,000) of NWs. Based on the photodetectors (e.g., the set of NWs within the photodetector) detecting light, the photodetectors may generate a certain current value and provide the current to the computing device via the LM nerve fiber 316. The computing device may receive the currents as well as the photodetectors that generated each of the currents. Then, the computing device may determine a pixel value associated with the current. For instance, the NWs within a photodetector may generate a current based on the detected light. The NWs may provide, via the connected LM nerve fiber of the photodetector, the current to the computing device. The computing device may sum or converge all of the currents for the NWs associated with the LM nerve fiber and/or the photodetector and use the summation of the currents to determine the pixel value. The image may be a gray-scale image and the current may resemble a certain shade (e.g., a luminance value) within the gray-scale. For example, the first photodetector may detect light and generate a current of 2 microamperes (μA) and the second photodetector may generate a current of 1 μA based on the amount of light shining on the photodetectors. The computing device may determine a luminance value of 200 nits based on the 2 μA for the first photodetector and 100 nits based on the 1 μA for the second photodetector. Then, the computing device may generate an image using the pixel values associated with the detected currents from the photodetectors of the EC-EYE 300 (e.g., the pixel in row 1, column 1 may have a pixel characteristic of 200 nits and the pixel in row 1, column 2 may have a pixel characteristic of 100 nits).

Additionally, and/or alternatively, the image may be a color image and the current may be converted to a red, green, blue (RGB) value. For instance, based on the currents from the photodetectors, the computing device may determine RGB values for the different pixels and generate an image using the determined RGB values. In some examples, to generate the color images, different materials (e.g., materials with different band-gap values) may be used for fabricating the EC-EYE 300 and/or the NW array 314.

In some instances, the LM wires 316 are behind the sensing material (e.g., the NW arrays 314), thus avoiding the aforementioned light loss and blind spot issue in human retina. In some examples, a 10×10 photodetector array (e.g., the NW array 314) may be fabricated with a pitch of 1.6 millimeters (mm). In some variations, the minimum size of each pixel within the image may be limited by the diameter of LM wire 316 of the photodetector, which may be a few micrometers (μm) or larger. In other variations, to further reduce pixel size, which increasing the spatial imaging resolution, another approach to fabricate sensor pixel array with each pixel area of around one $\mu m^2$ using metal microneedles may be used. This alternative approach is described in further detail below (e.g., described in FIG. 8B).

The light-sensing NWs 314 may be grown in a hemispherical template and thus a unique structure akin to human retina may be formed in one-step. Formamidinium lead iodide ($FAPbI_3$) may be used as the model material for NWs growth since it has excellent optoelectronic property and decent stability. However, in other examples, other suitable materials may be used as the model material for the growth of the NWs 314. The NWs 314 may be tightly embedded in the nano-template systematic characterization indicates their excellent crystal structure and optoelectronic properties. The NW growth and characterization details are described in further detail below. In other variations, other types of inorganic NWs made of Si, Ge, GaAs, and so on may also be grown using the vapor-liquid-solid process and used for the EC-EYE 300.

Figure 3C:
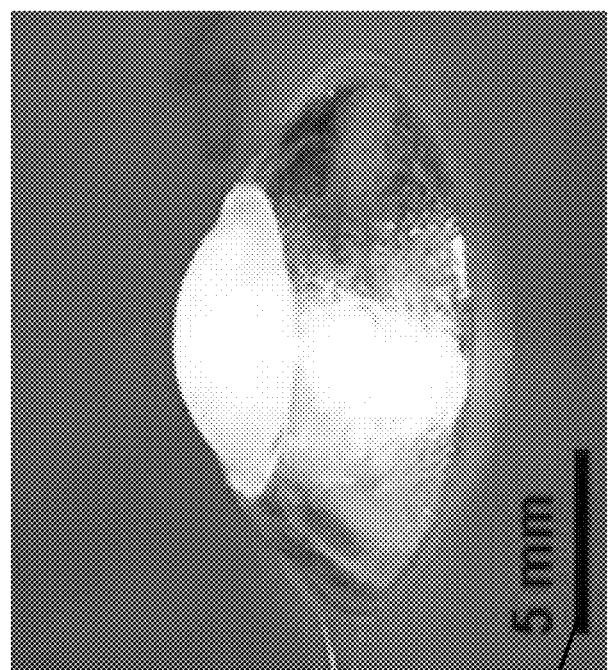
FIGS. 3B and 3C show different viewpoints of an assembled version of the EC-EYE from FIG. 3A.
Figure 3B:
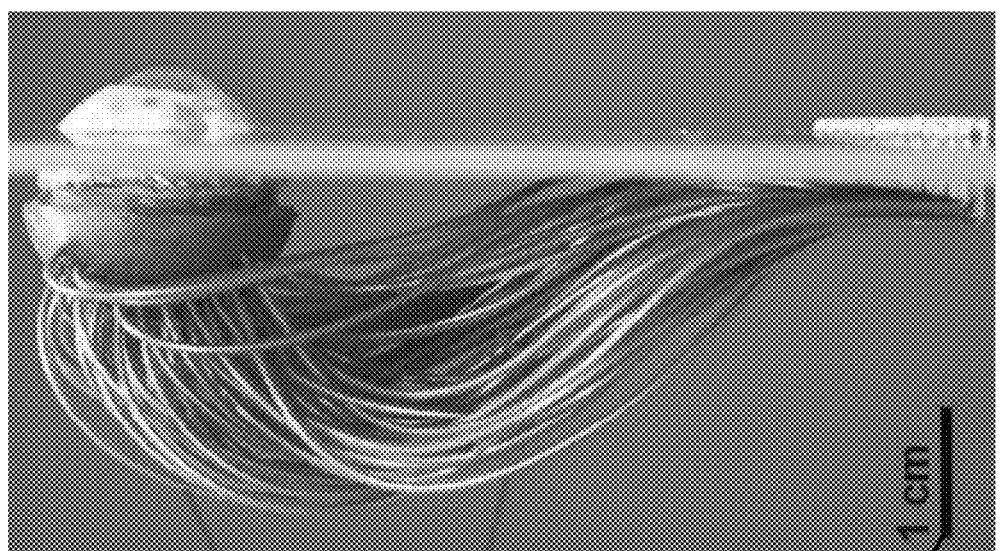

FIGS. 3B and 3C show different viewpoints of an assembled version of the EC-EYE from FIG. 3A. In particular, FIG. 3B shows a side-view of an assembled EC-EYE from FIG. 3A and an indicator 318 is shown to indicate one centimeter (cm). FIG. 3C shows a top-view of the assembled EC-EYE from FIG. 3A and an indicator 320 is shown to indicate five millimeters (mm).

Figure 4A:
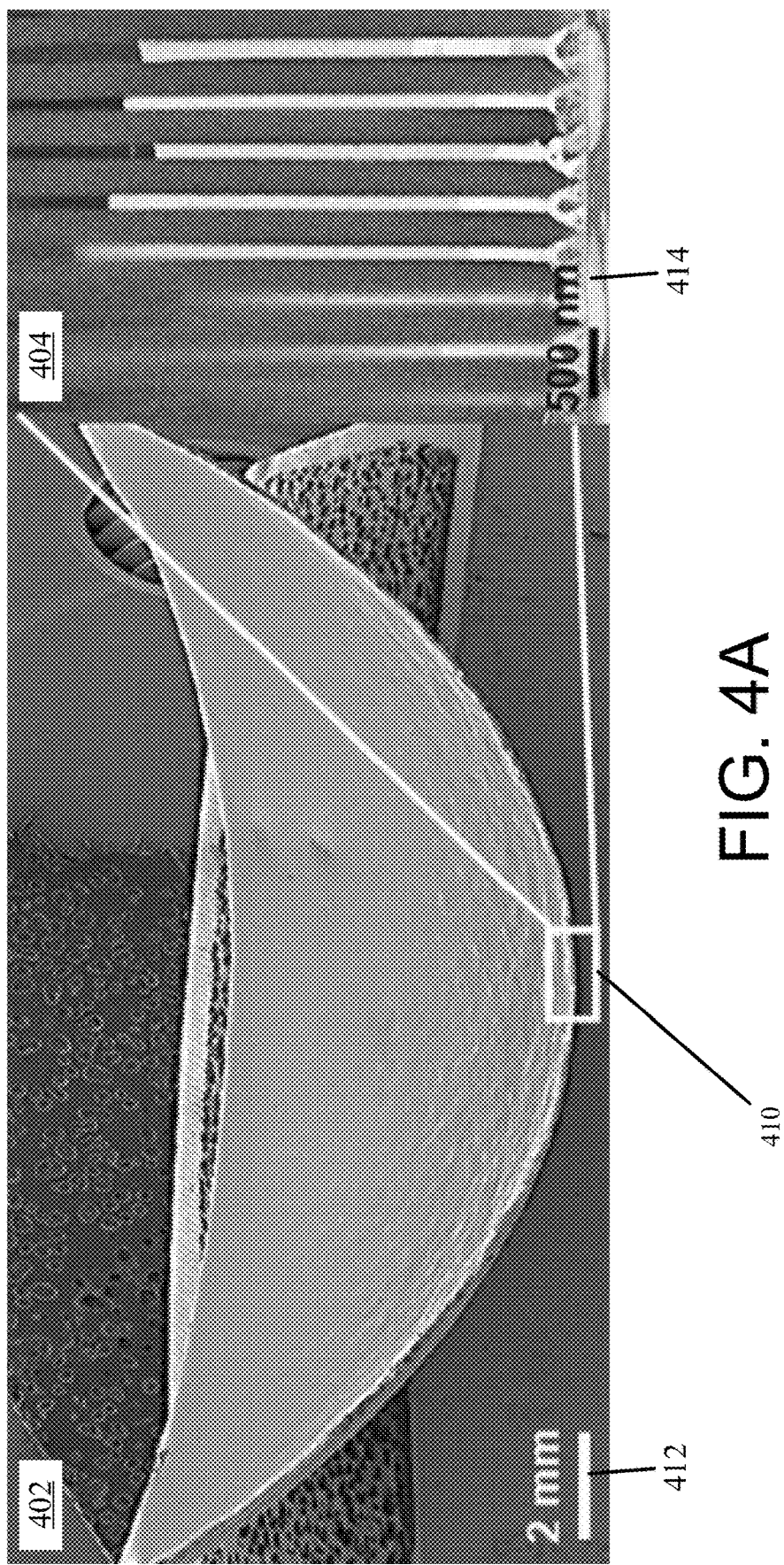
FIGS. 4A and 4B show images of some of the individual components of the EC-EYE from FIG. 3A.
Figure 4B:
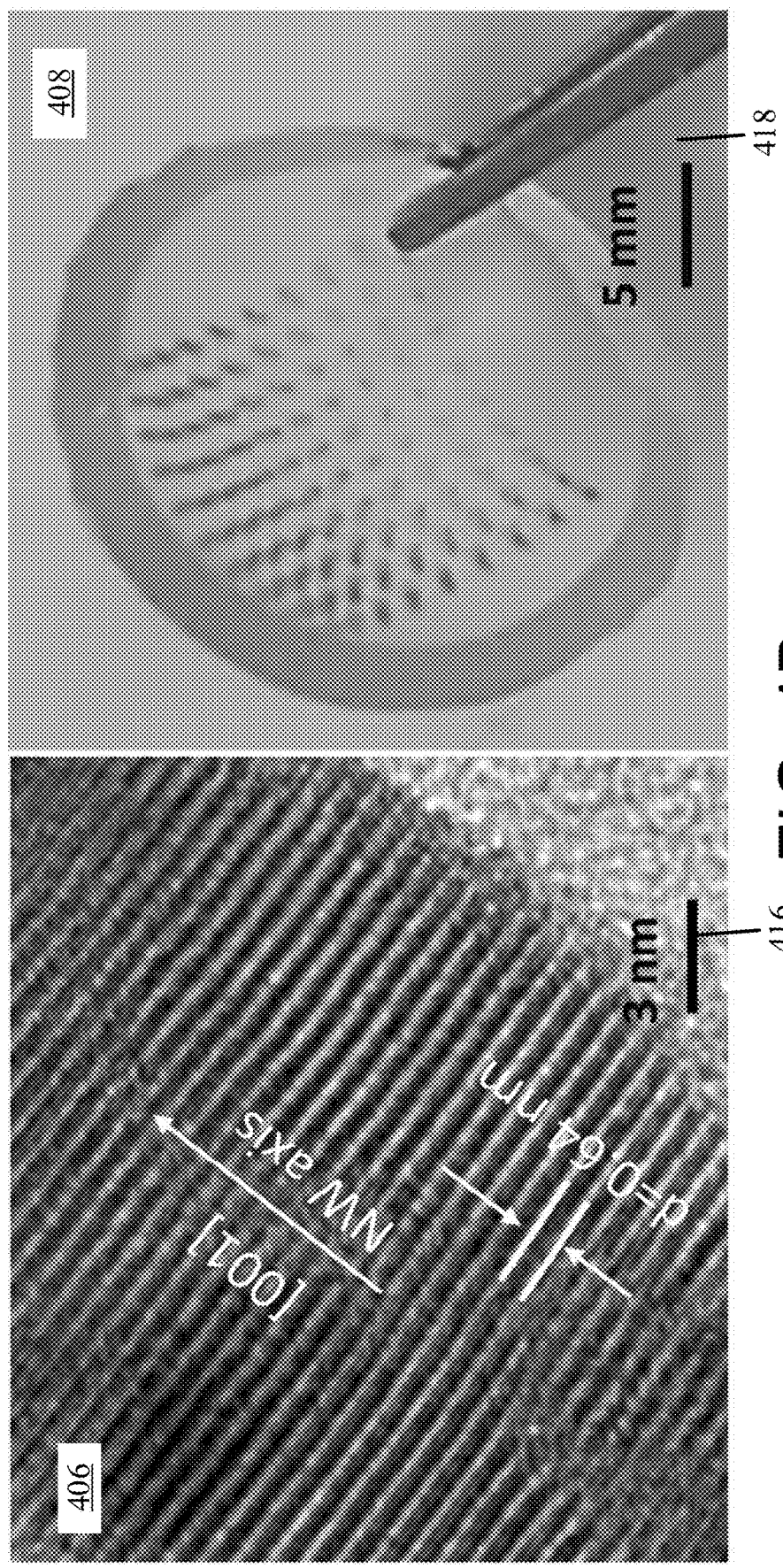

FIGS. 4A and 4B show some of the individual components of the EC-EYE from FIG. 3A in more detail. For instance, FIG. 4A and FIG. 4B has two sections each and each of the sections shows a different image of a component from the EC-EYE 300. Referring to FIG. 4A, section 402 is a low-resolution cross-sectional Scanning-Electron-Microscopy (SEM) image of the hemispherical PAM/NWs (e.g., the NW array retina 314). An indicator 412 is shown to indicate two mm. Section 404 is a cross-sectional SEM image of the NWs 314 in PAM. In particular, section 404 is a close-up image of the rectangular portion 410 denoted in section 402. The SEM images of the hemispherical PAM and NWs 314 shown in sections 402 and 404 are located at the bottom of the nano-channels. Referring to FIG. 4B, section 406 shows a high-resolution transmission-electron-microscopy (HRTEM) image of a single crystalline perovskite NW of the NW array 314 and shows the atomic structure of the NWs. In particular, the single crystalline NWs have 500 nm pitch and $4.6 \times 10^8$ cm$^{-2}$ density, which is much higher than that of photoreceptors in human retina, indicating a potency and/or capability to achieve high imaging resolution based on proper electrical contacts. The "[001]" within section 406 indicates the preferential growth direction of the nanowires and the "0.64 nm" is the inter-planar distance of adjacent crystalline planes. An indicator 416 is shown to indicate three nm. Section 408 shows an image of the PDMS socket 312 to assist the alignment of the LM wires 316. An indicator 418 is shown to indicate five mm. In the PDMS socket 312, there are many holes aligned into the high-density array. The LM fibers 316 may be inserted into the holes and thus are fixed by the PDMS socket, which yields a high-density LM fiber array.

Figure 5A:
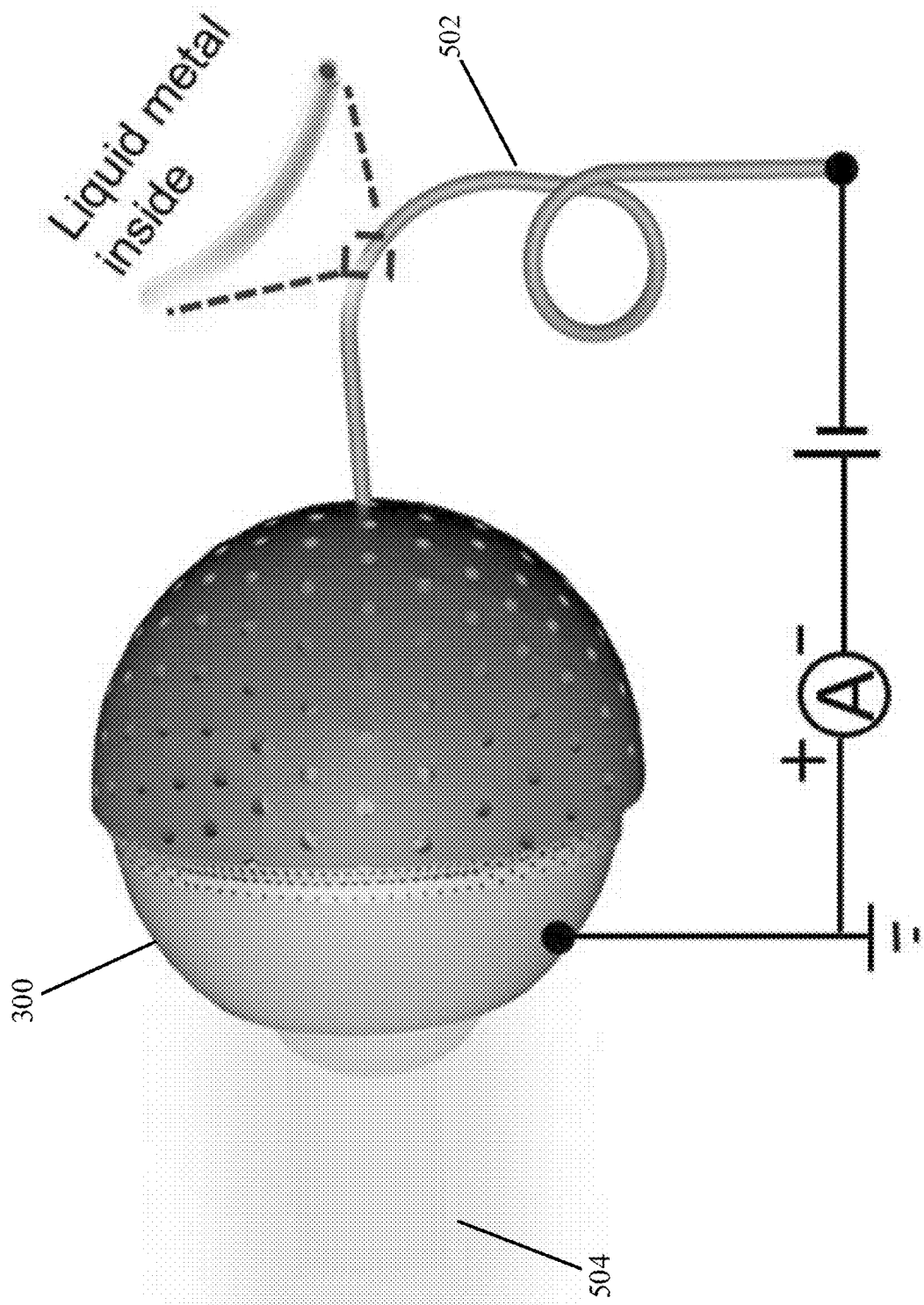
FIGS. 5A-5D show the photo-detection performance characterization of individual pixels using the EC-EYE 300 of FIG. 3A.

FIGS. 5A-5D show the photo-detection performance characterization of individual photodetectors using the EC-EYE 300 of FIG. 3A. For example, FIG. 5A shows an exemplary schematic of a single pixel measurement taken by the EC-EYE 300. In particular, FIG. 5A shows the EC-EYE 300, a single LM wire 502 that has liquid metal inside, and an electrical circuit (e.g., a ground, power source (e.g., an electrical cell or battery), and/or an ammeter/current meter. For instance, a collimated light beam 504 is focused on the pixels at the center of the retina of the EC-EYE 300. An individual photodetector within the EC-EYE 300 may detect the light and generate a current based on the light. The photodetector may provide the current on the single LM wire 502. As mentioned previously, a single photodetector may include, among other components, a single LM wire 502 and numerous (e.g., a subset of) NWs. In other words, each photodetector may be a dot within an image sensor (e.g., the NW array 314). When it is magnified, the surface of NW array 314 may appear like a large, dot-filled grid with each dot being a photodetector or a light receptor. Each of these dots are configured to provide for one pixel within an image. Additionally, and/or alternatively, each of these dots may be an independent photodetector comprising electrodes and sensing materials. As the photodetectors may share the same front electrode and the density of the NW array 314 is pretty high, the photodetector area may be defined by the back contact, which is the LM wire from the LM fibers 316. As such, the characteristics (e.g., luminance, RGB, and/or other pixel values) of a pixel from an image may be determined using a plurality of NW connected to an LM fiber 502.

Figure 5B:
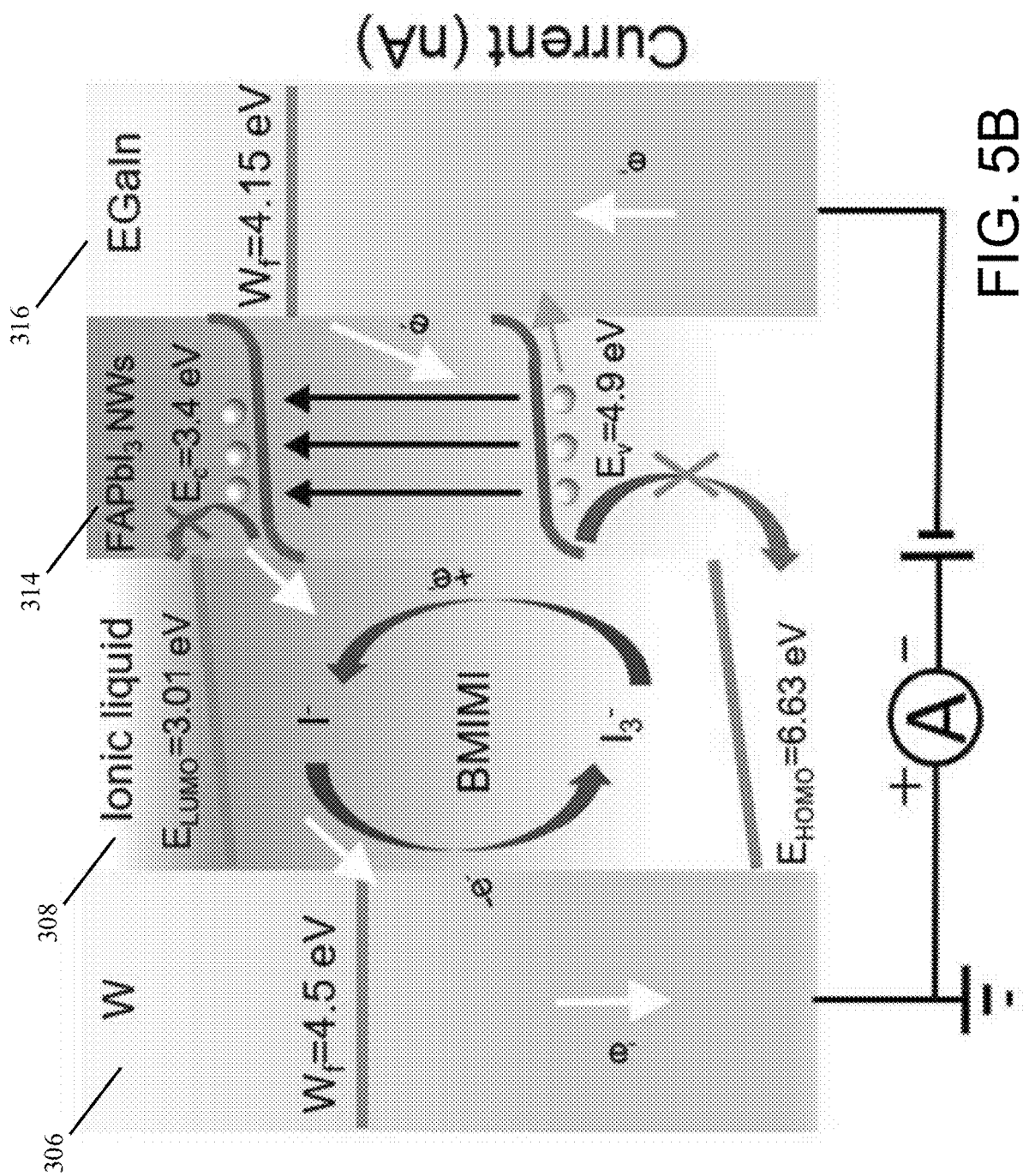

FIG. 5B shows the energy band alignment for the EC-EYE 300 and further shows the charge-carrier separation routes under light excitation. For example, FIG. 5B shows some of the components of the EC-EYE 300 such as the tungsten (W) film contact 306, the ionic liquid humour 308, the NWs from the NW array 314, and the LM wire 316 (e.g., the Eutectic-Gallium-Indium (EGaIn) LM wires). In operation, FIG. 5B shows the energy band diagram of an individual photodetector (e.g., the NW) under bias. The present application describes the materials used for the device. For instance, after contact, there are band bending at the interface due to the Fermi Level difference of the materials. Under bias, the energy band is tilted.

In operation, a beam of collimated light passes through the lens and electrolyte, then shines on the NWs. The NWs absorb the photon energy and generate electron-hole pairs. Due to the band bending and tilting, the holes move towards the LM electrode (e.g., the LM wires 316) and accumulates at the NW/LM interface. In the electrolyte, there are I$^-$ and I$_3^-$ serving as redox couples for the charge transfer from NWs 314 to tungsten electrode (e.g., the tungsten (W) film contact 306). The redox reactions can be described by the following formulas:

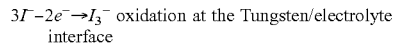
$3I^- - 2e^- \rightarrow I_3^-$ oxidation at the Tungsten/electrolyte interface

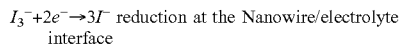
$I_3^- + 2e^- \rightarrow 3I^-$ reduction at the Nanowire/electrolyte interface The electrons at the Tungsten electrode 306 then travel along the external conduction wires and arrive at the liquid metal/NW interface (e.g., the interface between 314 and 316). At the interface, they recombine with the holes accumulated there to complete the current flow. Stronger light may correspond to more electron-hole pairs and further higher photocurrent. The light signals are thus detected by recording the amount of the current generated by this process.

Referring to FIG. 5B, $W_f$ indicates the work function of the material. $E_{homo}/E_{lumo}$ indicates the highest occupied molecular orbital (HOMO)/the lowest unoccupied molecular orbital (LUMO) levels of the electrolyte. They govern the thermodynamic stability of the electrolyte. BMIMI indicates the cation of ionic liquid. Its full name is 1-Butyl-3-methylimidazolium. $I^-/I_3^-$ are ions of iodine, serving as the redox couple in the electrolyte. $E_c$ is the conduction band edge of semiconductors. $E_v$ is the valence band edge of semiconductors.

In some instances, the EC-EYE 300 may capture the pixels of the images under a −3 Volt (V) bias voltage. The bias voltage may influence the whole band-gap for certain materials and/or components of the EC-EYE 300 as well as change the work function of the material. For instance, referring to FIG. 5B, the work function of the EGaIn (e.g., the LM fiber 316) is greater than the work function of W (e.g., the Tungsten electrode 306) based on the bias voltage.

Figures 5C, 5D:
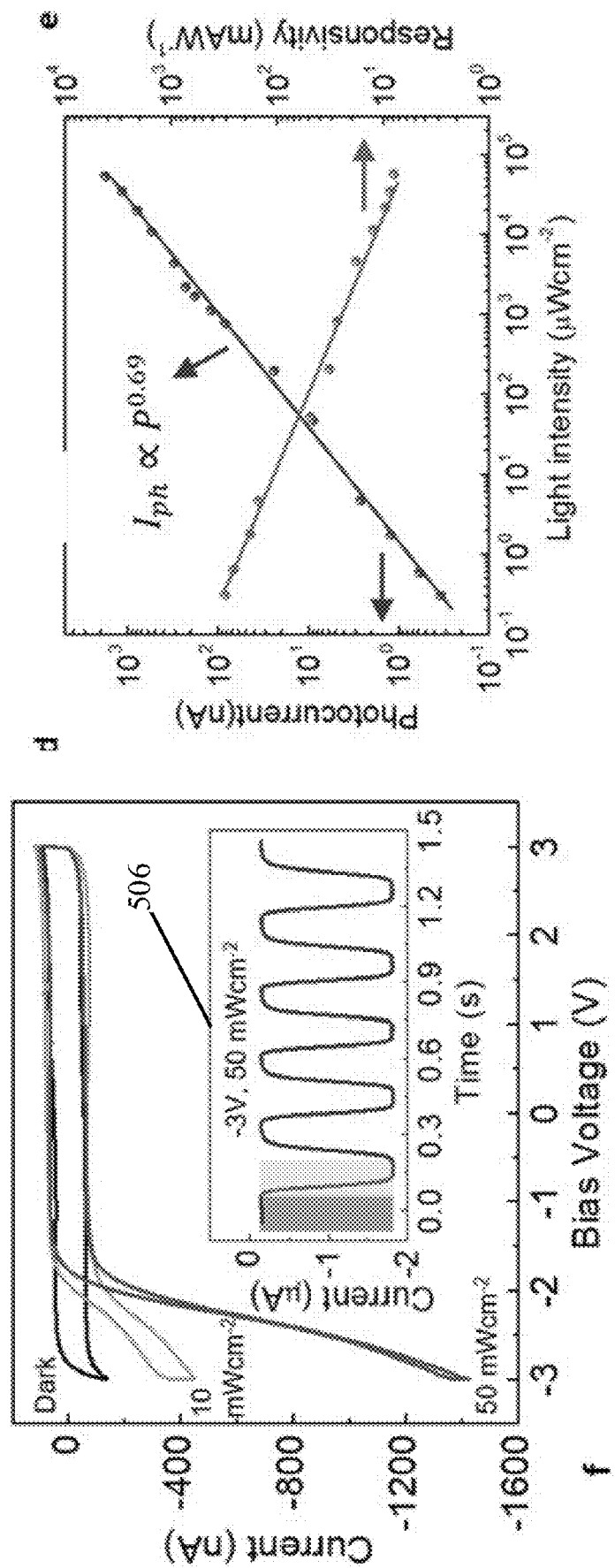

FIG. 5C shows the current-voltage (I/V) characteristics exhibiting asymmetric photo-response caused by asymmetric charge transportation at the two sides of NWs shown in FIG. 5B. The electrochemical characterizations indicate that the redox reactions of iodide ion/triiodide ($I^-/I_3^-$) pairs occur at the NW/electrolyte and tungsten film/electrolyte interfaces and ion transportation inside the electrolyte contribute to the photo-response. The inset 506 shows the transient response of the EC-EYE 300 to chopped light. The relatively fast and highly repeatable response indicates that the EC-EYE 300 has excellent photocurrent stability and reproducibility. The response and recovery time are around 32.0 milliseconds (ms) and 40.8 ms. Further, electrochemical analysis of the critical NW/electrolyte interface indicate the EC-EYE's 300 response time may depend on the kinetics of multiple types of ions at that interface. Electrochemical-impedance-spectroscopy (EIS) measurements indicate that EC-EYE's 300 structural optimization and ionic liquid concentration increase may substantially reduce the charge-transfer-resistance ($R_{ct}$) at the NW/electrolyte interface leading to reduction of EC-EYE's 300 response and recovery time down to 19.2 ms and 23.9 ms, which is much faster than that of human photoreceptors ranging from 40 ms to 150 ms.

The EC-EYE 300 may acquire the relatively fast and highly repeatable response speed by reducing the $R_{ct}$. For example, the EC-EYE 300 may be optimized by removing the sub-channel layer between NWs and metal electrodes. The barrier thinning process prior to NW growth may lead to the formation of fine sub-channels at the bottom of a PAM. NWs grown in this layer may have small diameter and higher resistance than the NWs in the main channels. As such, the EIS measurement shows $R_{ct}$ of the EC-EYE 300 is 5.56 and 1.89 Mega ohm under dark and light (50 milliwatts (mW) centimeter$^{-2}$ (cm$^{-2}$)). The EC-EYE's 300 response time and recovery time are 32 ms and 40.8 ms. In some examples, a mild ion milling process may be used to remove the sub-channel layer to facilitate carrier transport in NWs. For such examples, the $R_{ct}$ may be significantly dropped to 1.31 and 0.92 Mega ohm for dark and light condition, indicating the accelerated charge transfer process. As the result, the EC-EYE's response and recovery speeds ($t_{response}$=21.8 ms, $t_{recovery}$=29.9 ms) may be improved.

Additionally, and/or alternatively, increasing the concentration of I$^-$/I$_3^-$ redox couple (e.g., increasing the 1-Butyl-3-methylimidazolium iodide (BMIMI) concentration from 1 v % to 10 v % where v is volume and v % is a volumetric ratio) may further promote the charge transfer rate. Using these increased concentrations, the EIS measurement result indicates that the $R_{ct}$ has been further reduced to 1.28 and 0.4 Mega ohms under dark and light conditions, respectively. The response and recovery times have been reduced to 19.2 ms and 23.9 ms.

FIG. 5D shows the illumination intensity dependent photocurrent and responsivity of acquiring an individual pixel using the EC-EYE 300. The illumination light intensity shown on FIG. 5D has a large dynamic range from 0.3 μWcm$^{-2}$ to 50 milliwatts (mW) cm$^{-2}$. The photocurrent may be fitted with a quasi-linear power law relationship (I~P$^{0.69}$), where I is the photocurrent and P represents the irradiance power. The responsivity may increase when reducing illumination intensity and may reach up to 303.2 mAW$^{-1}$, which is among the highest in the reported photoelectrochemical (PEC) photodetectors. Under the lowest radiation level measured, the average number of photons received per second by an individual NW may be estimated as 86 photons. This sensitivity is at par with that of human cone cells. The corresponding specific directivity is calculated as ~1.1×10$^9$ Jones to 0.3 μWcm$^{-2}$ incident light. The spectral responsivity shows a broadband response with a clear cut-off at 810 nm. The stability and repeatability of an individual pixel under two hertz (Hz) continuously chopped light for nine hours was tested to confirm its durability. In other words, this indicates that although there are drifts for both dark and light currents, there is no obvious EC-EYE 300 performance degradation after 64,800 cycles.

Figure 6A:
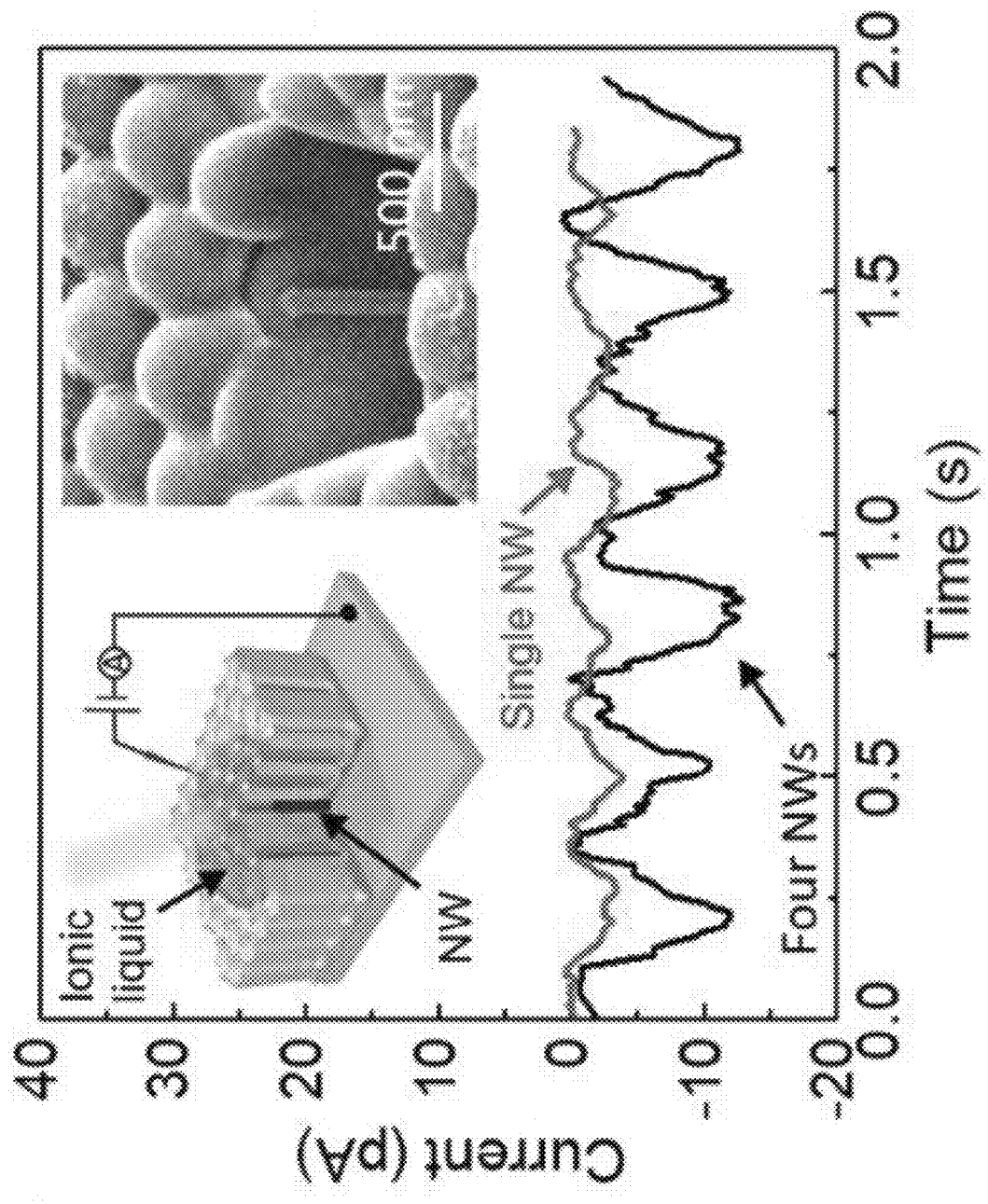
FIGS. 6A and 6B show an EC-EYE with single and multiple NW based electrochemical (EC) detectors as well as a fabrication process for the single and multiple NW based EC detectors.

As mentioned above, one of many advantages of using high-density NW arrays 314 for artificial retina is their potency toward high imaging resolution. Though the LM fiber contacts 316 described above to NWs 314 are convenient and image resolution is already at par with a number of existing bionic eyes in use, in some instances, the EC-EYE 300 may further be enhanced to reduce pixel size down to single-digit-micrometer level. For example, FIGS. 6A-B and 8A-C show additional and/or alternative examples of the EC-EYE 300 that are used to achieve an ultra-small pixel size. As shown in FIG. 6A, a single NW may be deterministically grown in a single nano-channel opened by focused ion-beam (FIB), which causes a single pixel with 500 nanometer (nm) lateral size and footprint of ~0.22 micrometer$^2$ (μm$^2$) to be captured.

Figure 6B:
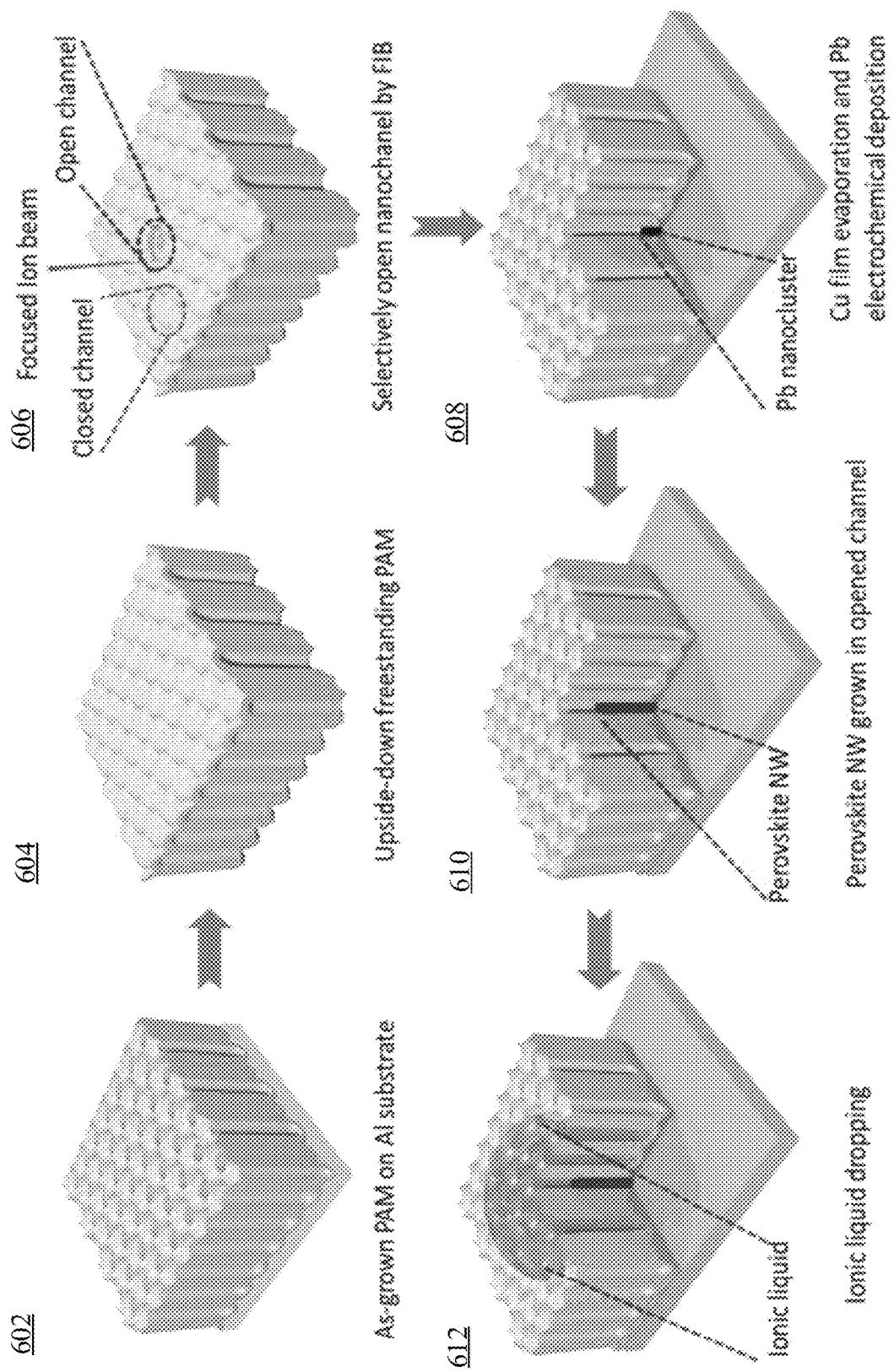

FIG. 6B shows a process 600 for fabrication of single and multiple NW based electrochemical (EC) detectors in further detail. In particular, FIG. 3A shows a spherical EC-EYE 300 with NWs and LM fibers 316. However, in some instances, the LM fibers 316 are unable to be scaled down to a small enough size (e.g., down to micron meters) for a desired resolution. Thus, FIG. 6B shows a process 600 to provide a greater resolution of images. In particular, as shown in FIG. 6B, the LM fibers 316 of EC-EYE 300 may be replaced by a Copper (Cu) electrode. Further, rather than growing the NWs in all the nanochannels, in FIG. 6B, the NWs are selectively grown in certain nanochannels. These single or multiple NWs may detect light and generate a current that gets passed through the Cu electrode for measuring, which generates a signal that is used for further imaging. In other words, rather than each LM fiber 316 being connected to a plurality of NWs and being associated with a photodetector, in FIG. 6B, all of the NWs may be connected via the Cu electrode and the current from single or multiple NWs may be used to determine the pixel characteristics of a pixel within an image. Since there are no NWs in most of the nanochannels, the functional area of photodetector is small, indicating a potency for high resolution. For instance, a single NW or multiple NWs (e.g., 4 NWs) may generate a current and this current from this single NW or multiple NWs may be used to determine a pixel characteristic for a pixel within an image. By using process 600, the pixel size of the image may be scaled to a very small area and thus is capable for ultra-high resolution. The process is based on a planar substrate rather than a hemispherical one as shown in FIG. 3A. The freestanding planar PAM was fabricated by standard two-step anodization followed by mercury (II) chloride (HgCl$_2$) etching. For instance, at stage 602, the Al substrate is anodized to form the PAM template (e.g. As-grown PAM on the Al substrate with "As-grown" meaning the template is fabricated by the two-step anodization process described above). At stage 604, the PAM template is peeled off the Al substrate and flipped to show its closed bottom. At stage 606, the freestanding PAM may be transferred into focused ion beam (FIB) to selectively etch away the barrier layer. To facilitate the etching, the chip may be bonded on an Al substrate with barrier layer side facing up. At stage 608, after FIB etching (e.g., with etching voltage: 30 kV, etching current: 26 nA), a 500 nm-thick Cu layer may be evaporated onto the barrier layer side to serve as the electrode for the subsequent lead (Pb) electrochemical deposition. Afterwards, at stage 610, the chip may be moved into a tubular furnace for perovskite NW growth. Then, a copper (Cu) wire may be bonded onto the Cu side of PAM by carbon paste and the whole chip may be fixed onto a glass substrate by UV epoxy. After curing, at stage 612, ionic liquid may be dropped onto the top of PAM. Additionally, and/or alternatively, a Tungsten probe may be inserted in the ionic liquid for photoelectric measurement. The photo-response may be measured with −3 V bias and 50 mW/cm$^2$ light intensity.

Figure 7:
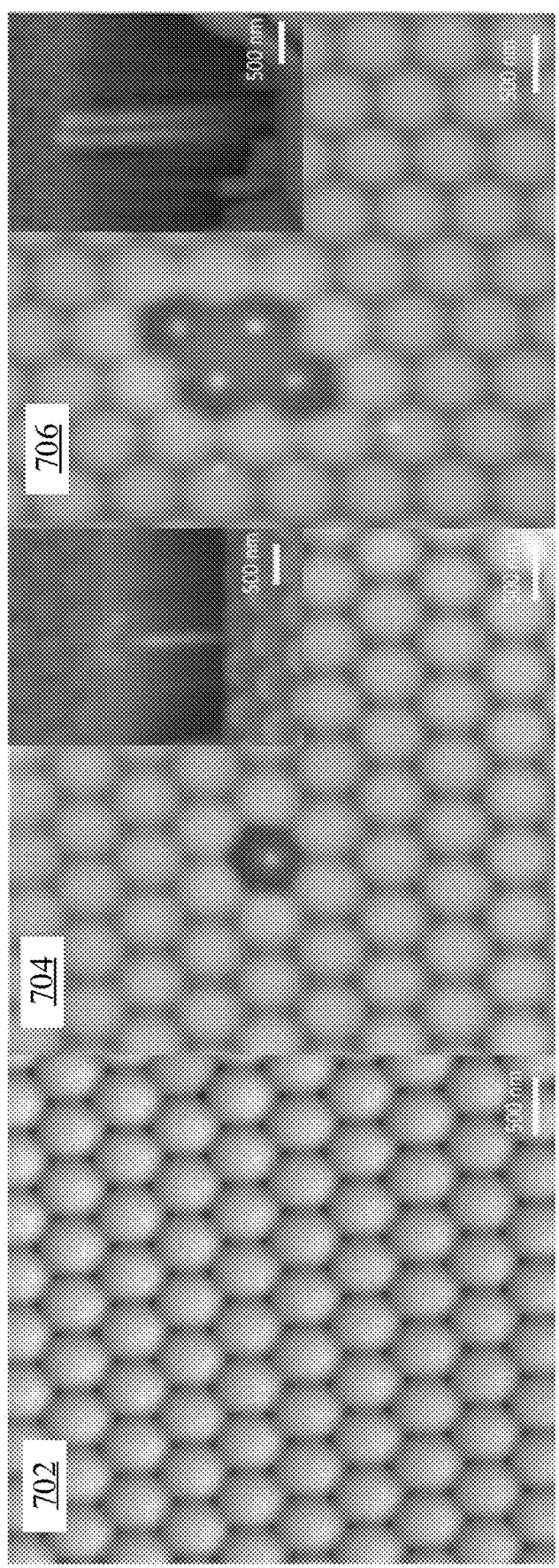
FIG. 7 shows scanning-electron-microscopy (SEM) images that show the controllable growth of nanowires (NW).

Using the same approach as shown in FIGS. 6A and 6B, a pixel of four NWs may also be fabricated and used to capture images. In other words, referring back to FIG. 3A, each photodetector, which includes a single LM fiber with numerous NWs (e.g., 1,500,000 NWs), may generate a current that is used to determine the pixel characteristics of a single pixel within an image. Using the approach in FIGS. 6A and 6B, four or fewer NWs may be used for a single pixel. For instance, each of the four NWs may generate a current based on the detected light and provide the currents via the Cu electrode to the computing device. The computing device may determine a pixel characteristic (e.g., luminance/RGB value) for a particular pixel based on the four NWs. For example, the computing device may sum up the four currents and based on the summation, may determine a particular pixel characteristic for a particular pixel (e.g., the value of the summation of the currents may relate to a particular pixel characteristic such as 100 nits). FIG. 7 shows SEM images that show the controllable growth of NWs, including the NW numbers and positions. In particular, FIG. 7 shows the top and cross-sectional view SEM images of PAM at different stages. For instance, stage 702 is before FIB etching, stage 704 is with single nanowire filled, and stage 706 is with four nanowires filled. Referring back to FIG. 6A, the photo-responses of these two devices (e.g., the single NW and the four NWs) are also shown.

Figure 8A:
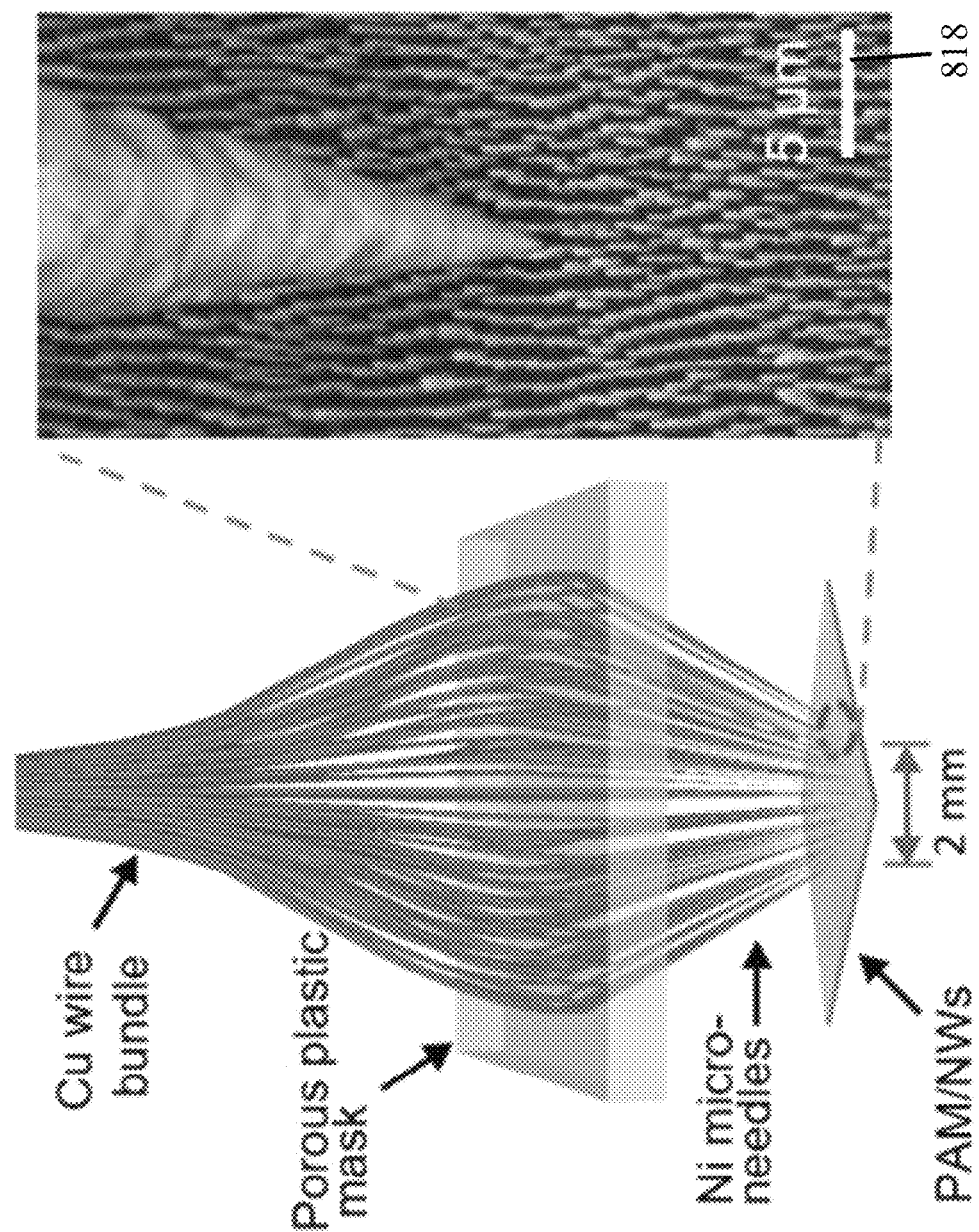
FIG. 8A-8C show an EC-EYE with microneedle contacts, a fabrication process of the microneedle array contacts, and viewpoints of the device structure after the fabrication of the microneedle array contacts.
Figure 8B:
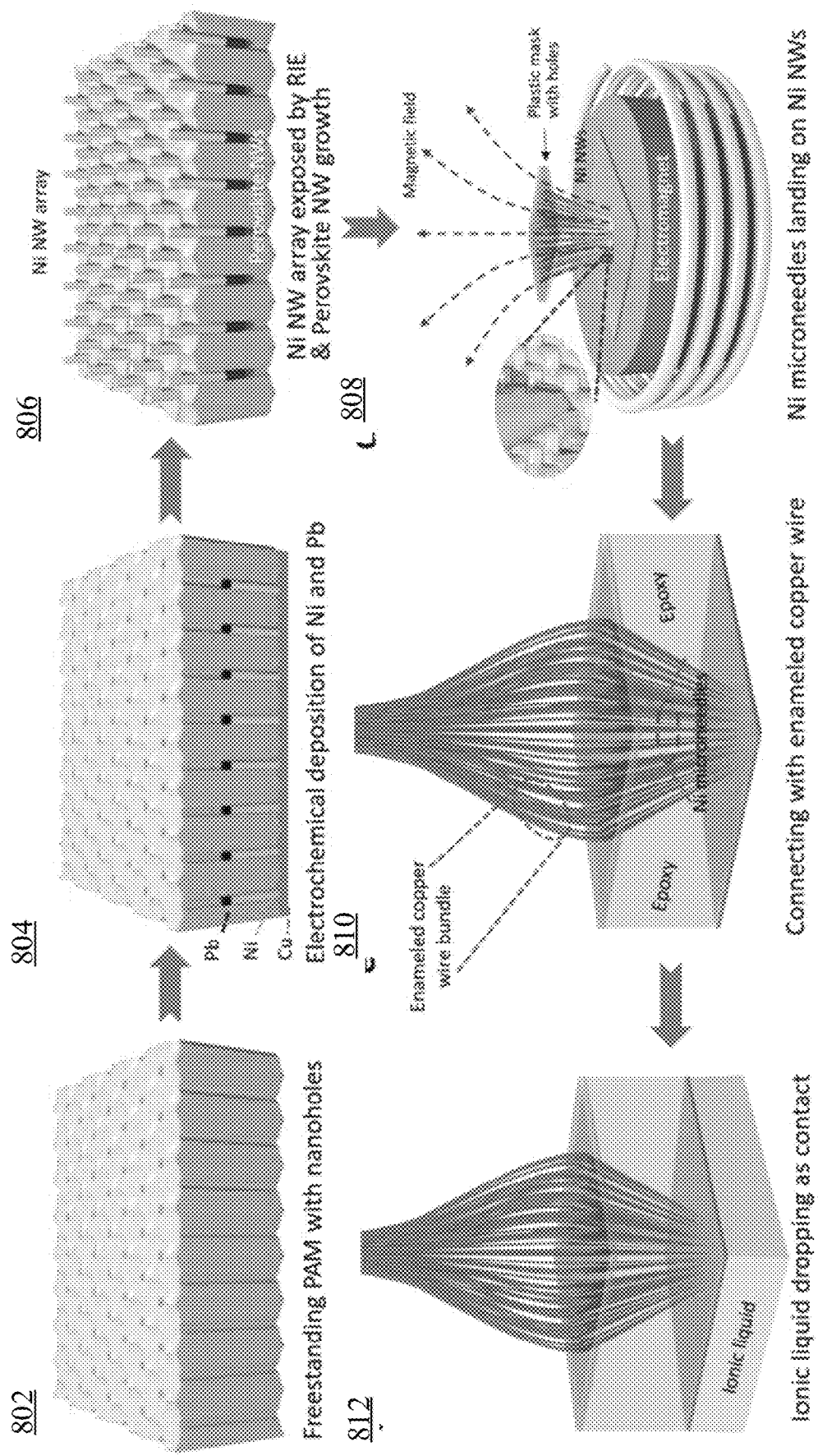
Figure 8C:
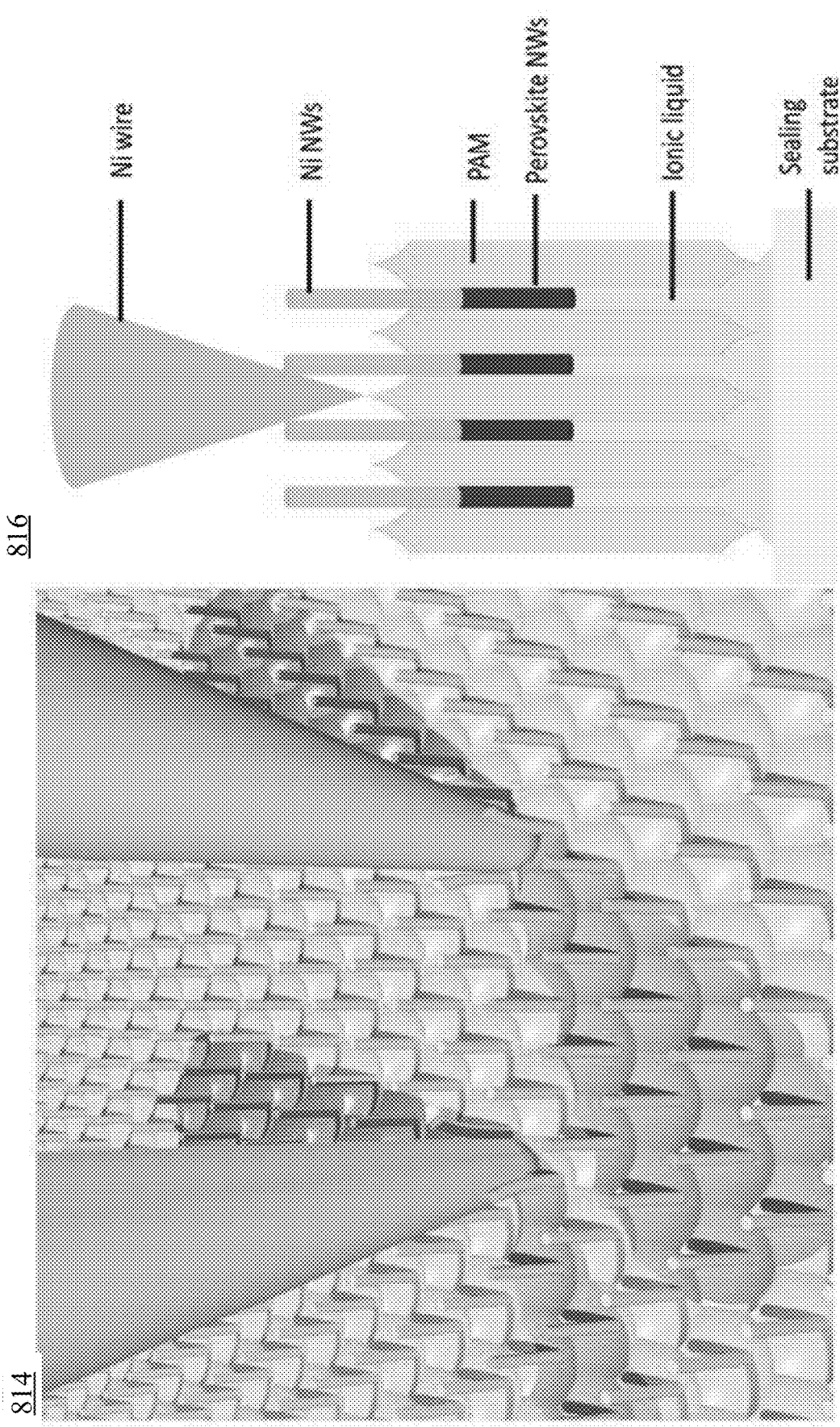

Instead of using the LM fibers 316, in some instances, microneedles (Nickel (Ni) microneedles) may be used to enhance and reduce the pixel size down to single-digit-micrometer level. In other words, the microneedles may replace the LM fibers 316 as the back contact that connects the NWs to the computing device. For instance, as mentioned previously, the LM fibers 316 may prove challenging to scale down to micron meters. Therefore, the microneedle back contacts may be used for smaller pixel integration. Each microneedle may be inserted into the NW array 314 and contacts only a few (e.g., 3) NWs within the array 314, which results in a small photodetector with only 3 NWs. In other words, the microneedles are the back contact and they provide the functionalities of the LM fibers 316 in FIG. 3A. Each microneedle may be used to determine a pixel characteristic of a pixel within the image (e.g., the computing device may receive currents from the 3 NWs associated with a particular microneedle and use these currents to determine a pixel characteristic for a particular pixel associated with the 3 NWs/the microneedle). FIGS. 8A-8C show the schematic using Ni microneedle contacts to the NW array 314 as well as the process of fabricating the microneedle contacts. For instance, FIG. 8A schematically shows the EC-EYE 300 coupled to the copper (Cu) wires signal transmission lines. The lateral size of the contact region may be 2 mm. For example, to form an array of ultra-small pixels, Ni microneedles may be vertically assembled on top of a PAM by magnetic field and thus each microneedle can address three NWs forming a pixel with lateral size of around 1 μm and pitch of 200 μm. The indicator 818 shows 5 μm.

FIG. 8B shows the schematic fabrication process of integrated electrochemical image sensor based on microneedle array contacts assisted with magnetic field. Stage 802 shows the freestanding PAM with through pores. For example, freestanding PAM of 40 μm thick may be fabricated by standard anodization process, Sodium hydroxide (NaOH) etching and Mercury (II) Chloride (HgCl$_2$) solution etching. Ion milling may be used to remove the barrier layer to achieve through-hole PAM. Then, stage 804 shows the Pb and Ni NW grown in the PAM. For example, Copper (Cu) film of 1 μm thick may be thermally evaporated onto the through-hole PAM to serve as the electrode for the subsequent Ni and Pb electrochemical deposition. Stage 806 shows the perovskite NWs grown in the PAM and Ni NW exposed by RIE. For example, to expose the Ni NWs, the copper layer may be removed by ion milling and the PAM may be partially etched away by Reactive Ion Etching (RIE). The exposed Ni nanowires may be about 3 μm long. The chip may be moved into tubular furnace for perovskite NW growth. After, stage 808 shows a magnetic field assisted assembly of Ni micro-wires on Ni NWs/PAM. For instance, the PAM chip may be fixed on an electromagnet with Ni nanowires facing upward. Meanwhile, Ni micro-wires of 50 μm diameter may be sharpened in a mixed acidic solution (100 ml 0.25M hydrochloric acid (HCl) aqueous solution+ 100 ml ethylene glycol (EG)) under the bias of 1 V, with Ni micro-wires as working electrodes and tungsten coil as counter electrode. The resulted Ni micro-wires may be sharp tips, with curvature radius ranging from 100-200 nm. The Ni needle may then gently be landed onto the PAM substrate with the magnetic field ON. Due to the magnetic force, the ferromagnetic Ni microneedles can engage into the Ni NW forest to form effective electrical contact to NWs. To facilitate Ni micro-wire landing, a mask with 10×10 hole array (hole diameter: 100 μm, pitch: 200 μm) may be used to align the Ni microneedle. Stage 810 shows the epoxy packaged device. Stage 812 shows the device with ionic liquid for measurements. For example, after landing, UV epoxy may be dropped between the mask and PAM substrate. Copper enameled wire with diameter of 60 μm may be inserted into the hole to form electrical contact bridging the Ni microneedle and external PCB board.

FIG. 8C shows different views of the device structure after it has been fabricated using the process described in FIG. 8B. For example, view 814 is a top view of the device structure and view 816 is a side view of the device structure. As shown, the device includes the Ni needles, the Ni NWs, the PAM, the perovskite NWs, the ionic liquid, and a sealing substrate.

Figure 9:
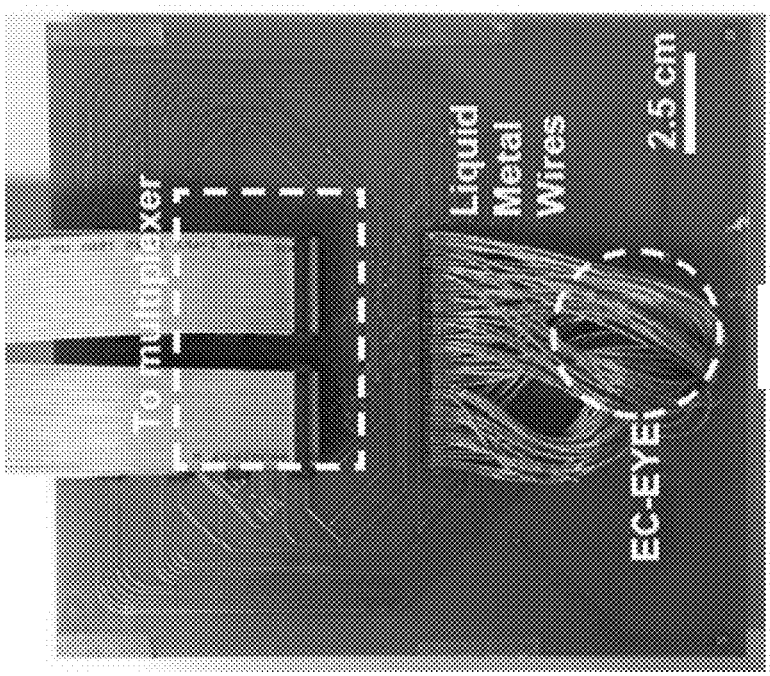
FIG. 9 shows different viewpoints of the EC-EYE from FIG. 3A.
Figure 9:
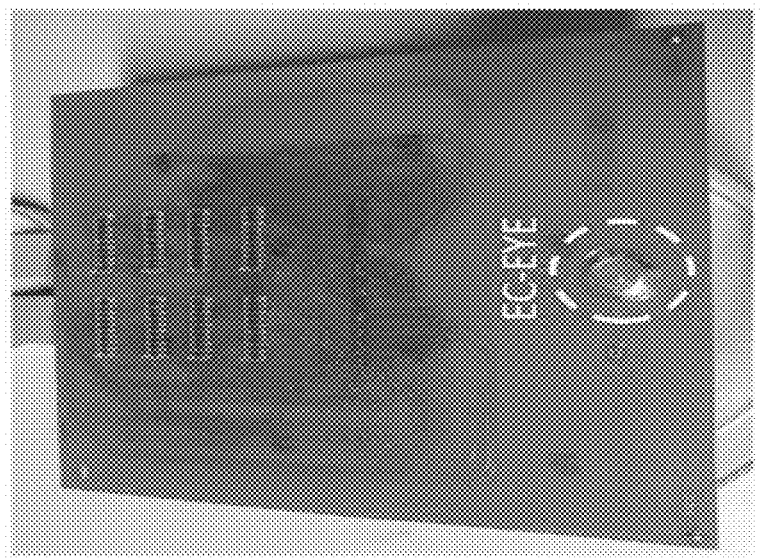
Figure 9:
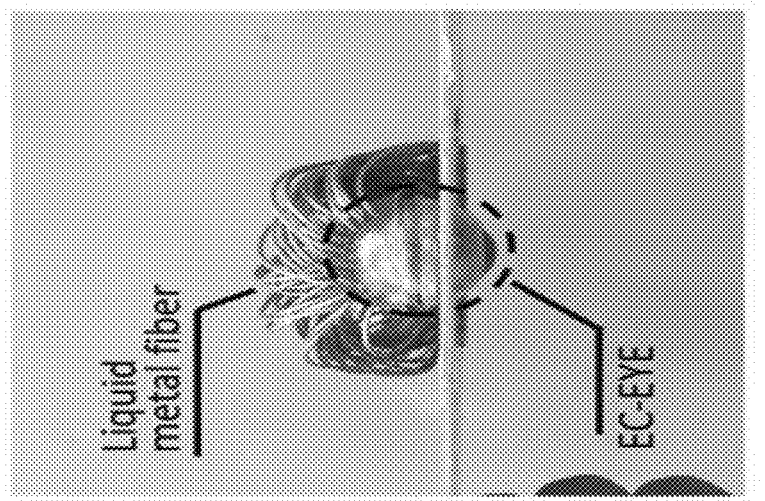

After characterization of individual photodetectors above, the functionality of the full device imaging system will be described below. FIG. 9 shows different viewpoints of the EC-EYE 300. For example, viewpoint 902 shows a side-view of the EC-EYE (e.g., EC-EYE 300) with the liquid metal fibers (e.g., the LM nerve fibers 316). Viewpoint 904 shows a front-view of the EC-EYE that is mounted onto a printed circuit board (PCB). Viewpoint 906 shows the back-view of the EC-EYE with the liquid metal wires/fibers. Furthermore, viewpoint 906 also shows a multiplexer that is electrically coupled to the LM wires/fibers. While the example shown on FIG. 9 includes the PCB, the PCB may be optional in other instances (e.g., the EC-EYE may be used without a PCB).

Figure 10A:
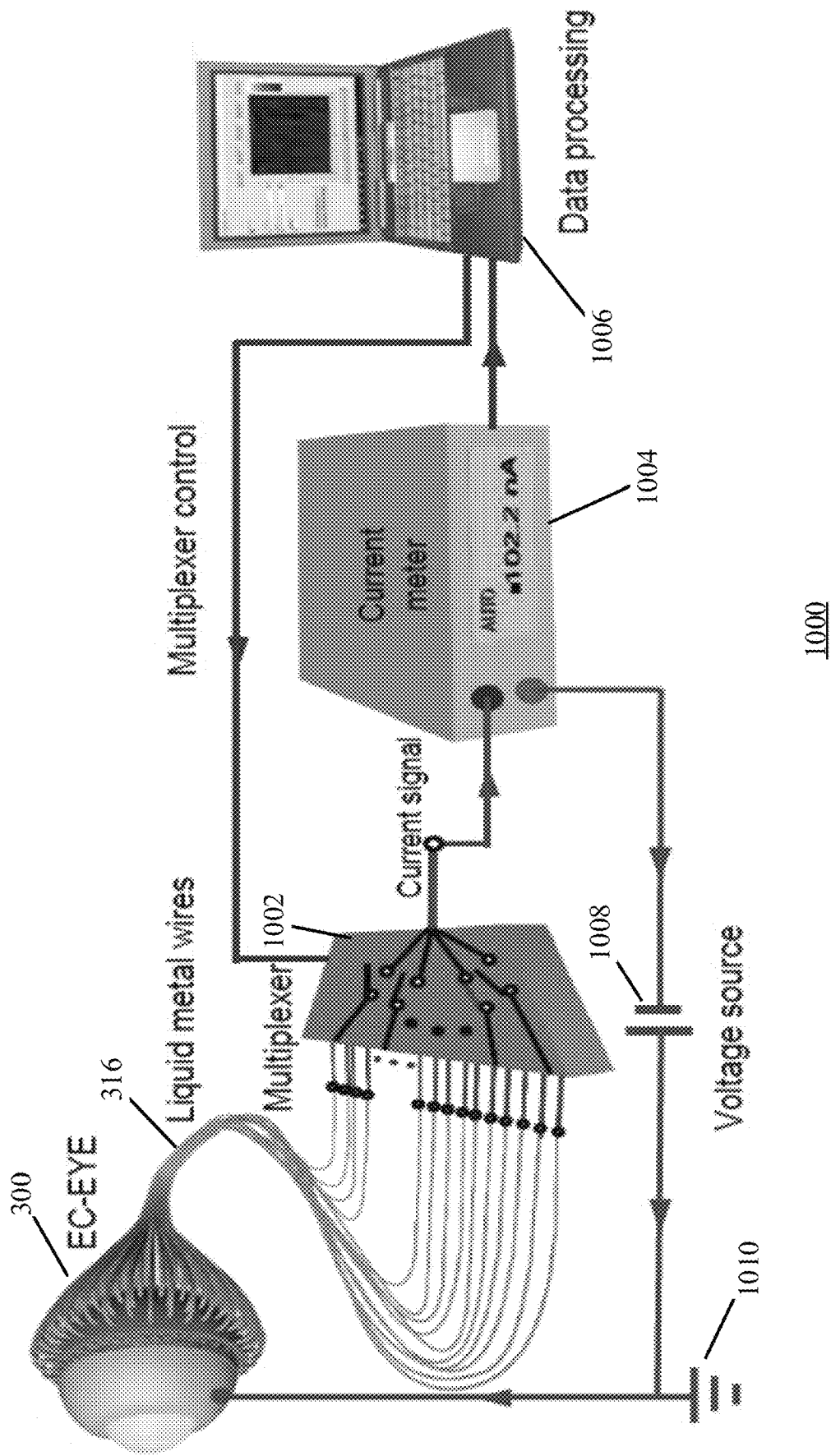
FIGS. 10A-10C show an exemplary system and an exemplary circuit diagram that uses the EC-EYE to capture images as well as an image captured using the EC-EYE.
Figure 10B:
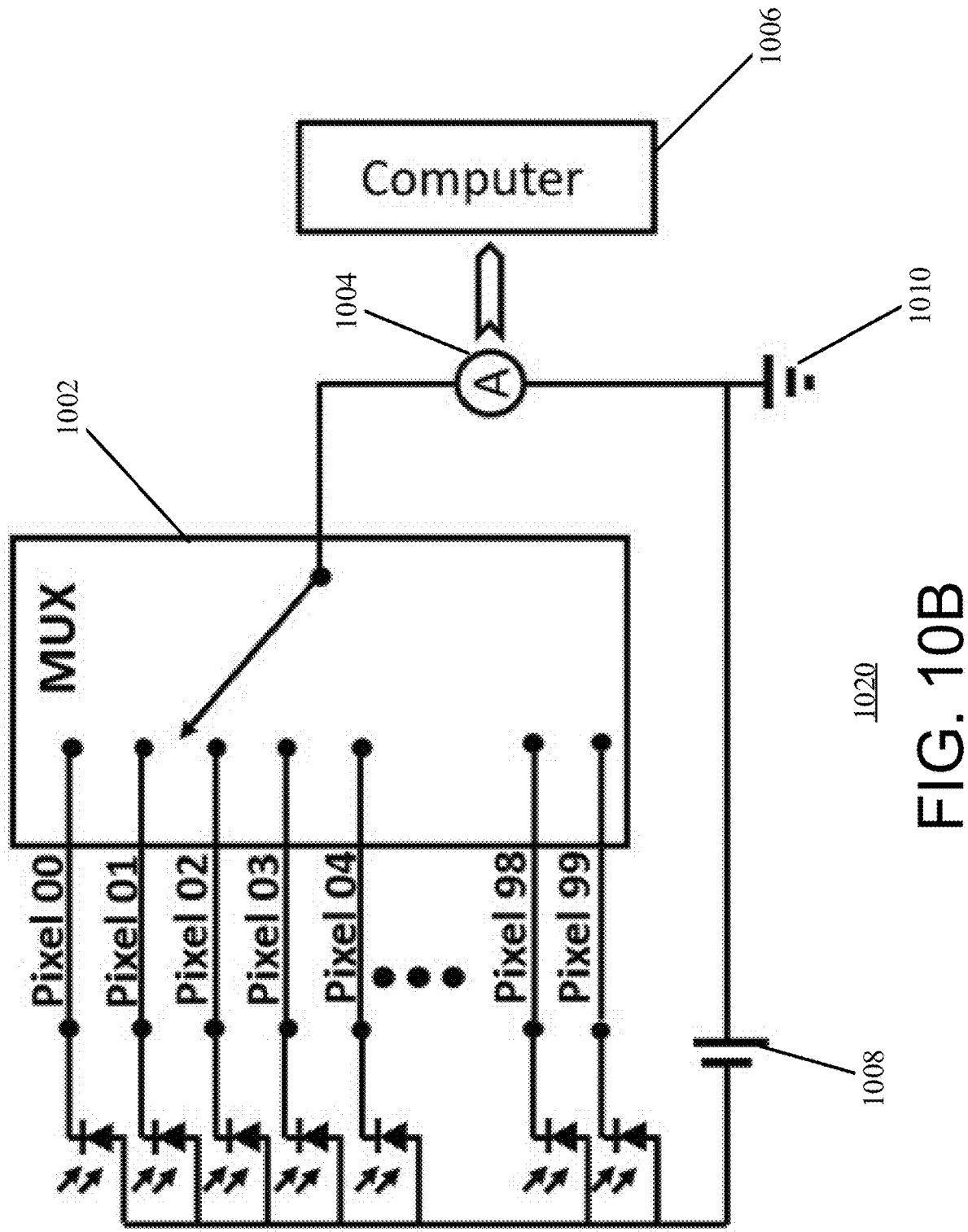

FIG. 10A shows an exemplary system 1000 that uses the EC-EYE to capture images. For example, the EC-EYE 300 includes the LM wires 316. The LM wires 316 are connected to a controllable 100×1 multiplexer 1002 via a PCB. The PCB and multiplexer 1002 are shown in FIG. 9. The system 1000 further includes a current meter 1004 (e.g., ammeter), a computing device 1006 for data processing, a voltage source 1008, and ground 1010. The multiplexer 1002 is an electrical component with multiple input channels and one output channel. In operation, the selected inputs within the multiplexer 1002 are connected to the output. Each input channel is connected with one photodetector (e.g., one LM nerve fiber) of the EC-EYE 300. The selected photodetector forms a complete circuit with the current meter 1004 and the current of this photodetector is recorded. The position information, which is the channel number, of this photodetector is also recorded. The current is proportional to the light intensity. By scanning or determining the inputs for all the photodetectors, the light intensity distribution may be recorded by the computing device. Therefore, the system may record/determine the incident image based on the currents and the position information (e.g., the channel number) of the multiplexer 1002. FIG. 10B shows a circuit diagram 1020 of the system 1000. For instance, circuit diagram 1020 also includes the multiplexer 1002, the current meter 1004, the computing device 1006, the voltage source 1008, and ground 1010. Additionally, each of the pixels (e.g., "Pixel 00" to "Pixel 99") denotes a different LM wire from the LM wires 316. In some instances, such as the EC-EYE produced using a Cu electrode (e.g., FIG. 6B), the EC-EYE might not have LM fibers 316 and may have a single Cu electrode. Accordingly, the Cu electrode may connect directly to the current meter 1004 (e.g., the multiplexer 1002 might not be used in such a system). In some examples, such as the EC-EYE produced using the microneedles shown in FIG. 8B, the EC-EYE might not have LM fibers 316 and may have a plurality of microneedles. Each of the microneedles are connected to an input of the multiplexer 1002. In some variations, the input channels of the multiplexer 1002 may be associated with a particular pixel to be rendered in an image. For instance, the first channel may be associated with a pixel in column 1, row 1 (e.g., "Pixel 00" shown in FIG. 10B) and the second channel may be associated with a pixel in column 1, row 2 (e.g., "Pixel 01" shown in FIG. 10B. Using the currents and the associated channel from the multiplexer 1002, the computing device may determine the pixel characteristic as well as the location of the pixel within the image for the pixel characteristic.

Figure 10C:
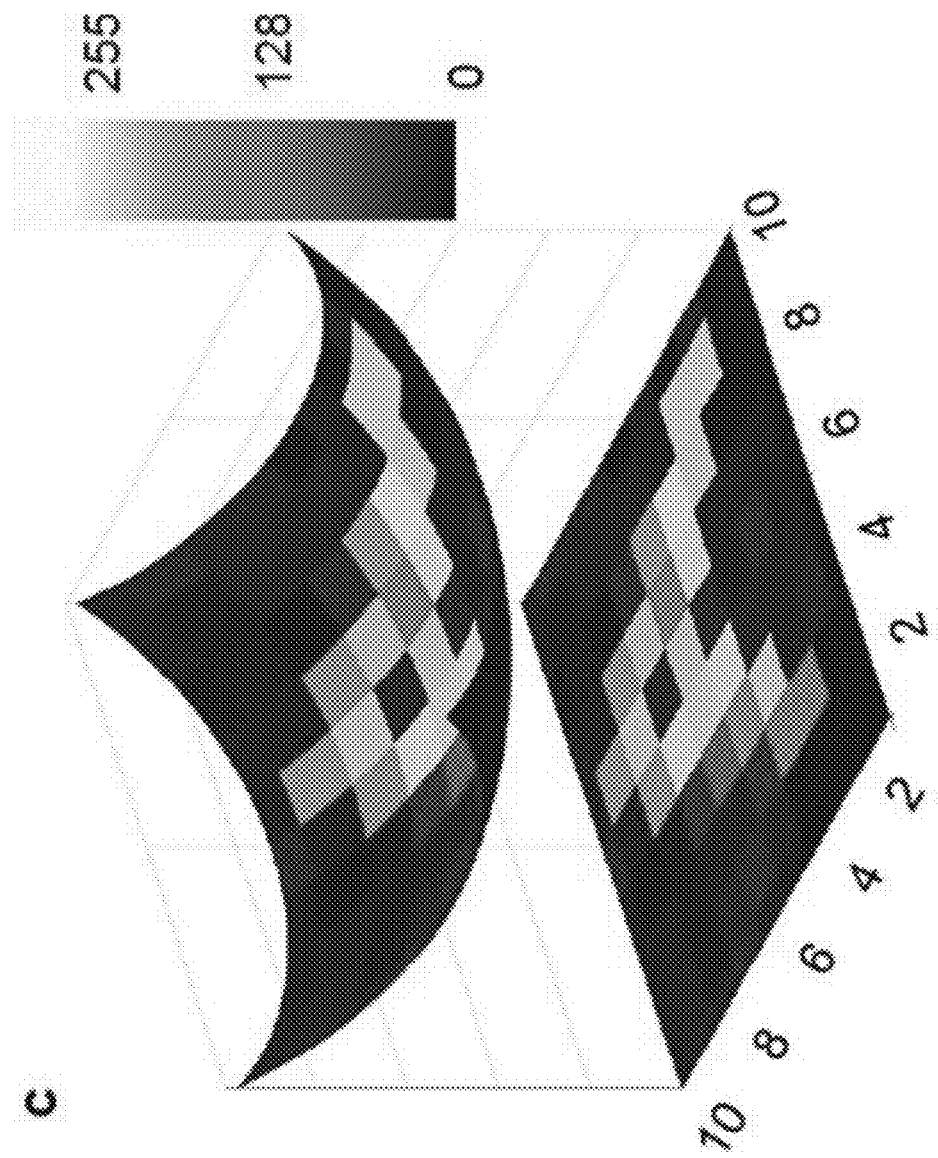

By projecting optical patterns, the EC-EYE 300 may record, identify, and/or acquire the photocurrent of each sensor pixel. In some examples, to reconstruct the optical pattern projected on the EC-EYE 300, the photocurrent value may be converted to grayscale number between 0 and 255. The equation used for grayscale conversion is the following:

$$G=(I_{Light}-I_{Dark})/(I_{Full}-I_{Dark})\times 255 \qquad \text{Eq. (1)}$$

where G is the grayscale value, $I_{Full}-I_{Dark}$ gives the dynamic range as the difference between the full light condition current and the dark current of a pixel. FIG. 10C shows the imaged character "A" and its projection on a flat plane using the EC-EYE 300 and the system 1000.

Compared to planar image sensors based on crossbar structure, the EC-EYE 300 may deliver higher contrast with clearer edges since each individual pixel is better isolated from the neighboring pixels. In some instances, rather using an EC-EYE 300 with LM contacts 316, a small EC image sensor with microneedle contacts may also be fabricated as mentioned above and used to capture images. In some examples, a high precision robotic arm enhanced with a piezo actuator may be used to land the Ni microneedles on the hemispherical PAM, assisted by magnetic field and a high-resolution optical monitoring system.

Figure 11:
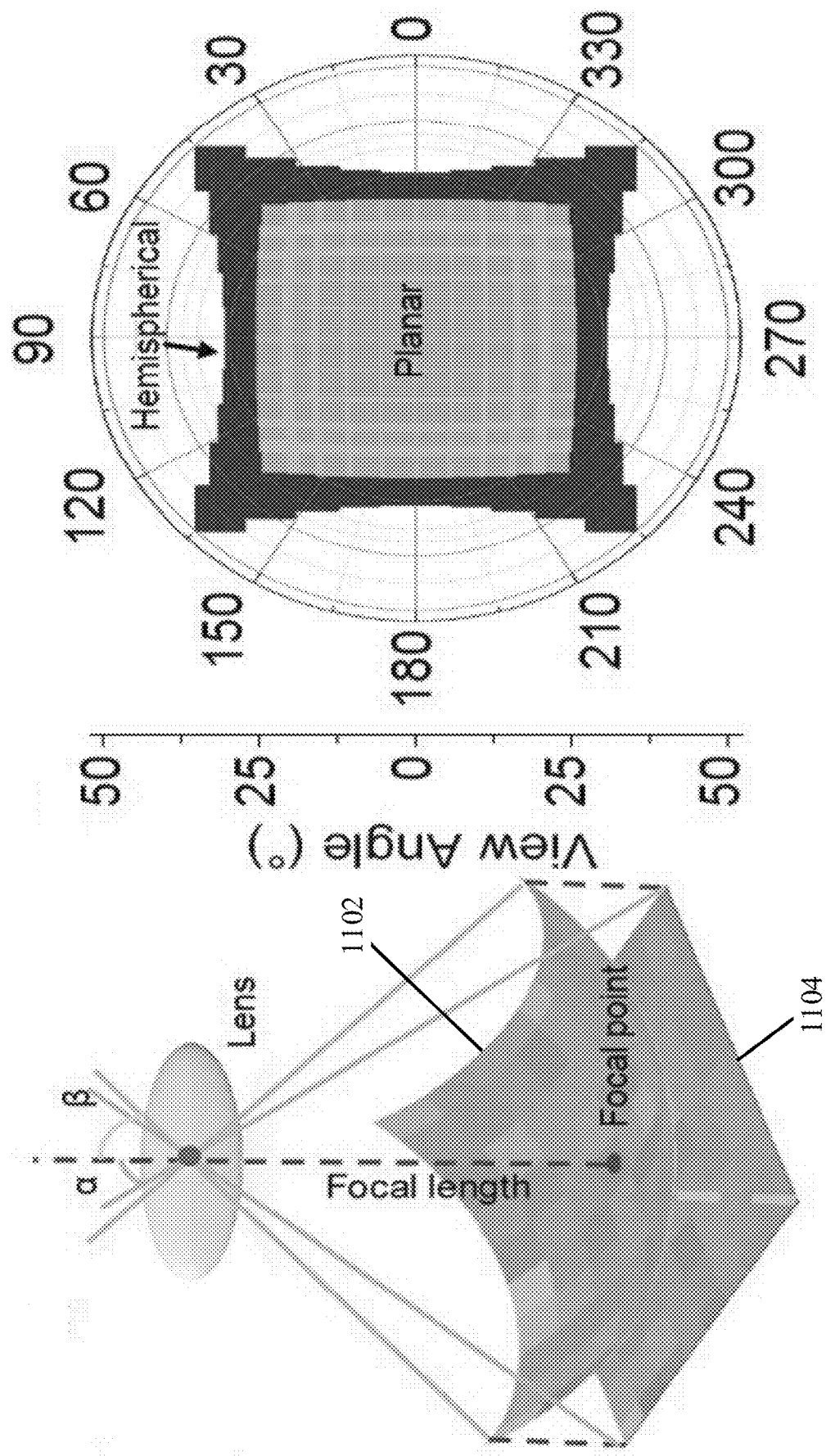
FIG. 11 shows a comparison of the FOV between the EC-EYE and a planar image sensor.

FIG. 11 shows a comparison of the FOV between the EC-EYE 300 and a planar image sensor. For example, compared to a planar image sensor, the hemispherical shape of the EC-EYE 300 ensures a more consistent distance between pixels and lens, resulting in a wider FOV and better focusing on all pixels. For instance, the top layer 1102 is hemispherical in shape and as such, the distance between the center and the edges/corners are more consistent. The bottom layer 1104 is from a planar image sensor, which shows that the distance from the center to the edges/corners to be inconsistent. The diagonal visual field of our hemispherical EC-EYE is 100.1° while that of a planar device is only 69.8°. Moreover, this angle-of-view can be further improved to approach the static vertical FOV of a single human eye (around) 130° without considering the eye/head movement, by optimizing the pixel distribution and the shape of PAM beyond hemisphere.

As disclosed herein, a biomimetic eye (e.g., the EC-EYE 300) with a hemispherical retina made of high-density light-sensitive NWs is used to capture images. The EC-EYE 300 may have a structure with high degree of similarity to that of a human eye while with a potency to achieve higher imaging resolution based on the examples and enhancements above. The developed processes may tackle the bottleneck challenge on fabricating optoelectronic devices on non-planar substrates with high integration density. Furthermore, the EC-EYE 300 may be used by a wide spectrum of technological applications such as in scientific instrumentation, consumer electronics, robotics, and so on.

Figure 12:
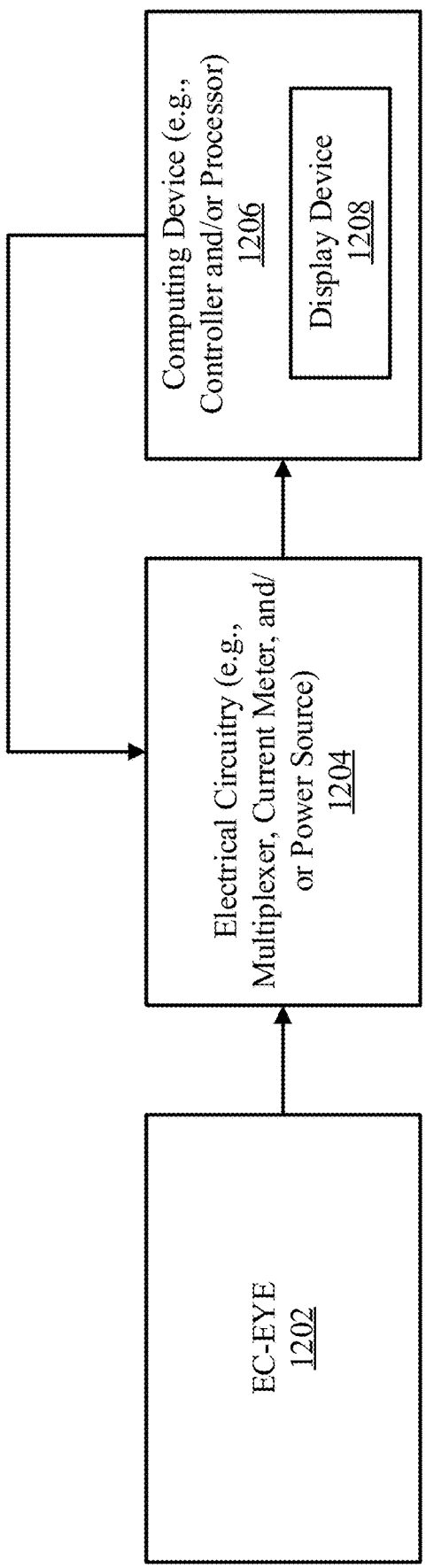
FIG. 12 is a schematic diagram of an exemplary system for using the EC-EYE to capture one or more images.

FIG. 12 is a schematic diagram of an exemplary system 1200 for using the EC-EYE to capture one or more images. For example, the system 1200 includes an EC-EYE 1200, electrical circuitry 1204, and/or a computing device 1206 with a display device 1208. Although the entities within system 1200 may be described below and/or depicted in the FIGS. as being singular entities, it will be appreciated that the entities and functionalities discussed herein may be implemented by and/or include one or more entities. For example, in some instances, the display device 1208 may be a separate entity from the computing device 1206. In other words, the computing device 1206 may be one or more controllers and/or processors that are configured to perform image processing based on the information from the EC-EYE 1202 and/or the electrical circuitry 1204.

In some instances, the system 1200 may be a block diagram of the system 1000 shown in FIG. 10A. The EC-EYE 1200 may be the EC-EYE 300 and/or an EC-EYE with microneedles, the computing device 1206 may be the computing device 1006, and the electrical circuitry 1204 may include the multiplexer 1002, the voltage source 1008, the current meter 1004, and the ground 1010. In other instances, the system 1200 may include one or more components/entities from system 1000 and/or may further include one or more additional and/or alternative components/entities that are not shown in system 1000.

The EC-EYE 1202 may be designed and/or include similar functionalities to the EC-EYE 300 described above. For example, the EC-EYE 1202 may include an NW array retina (e.g., the NW array retina 314), LM nerve fibers (e.g., the LM nerve fibers 316), and/or the additional/alternative components described above in FIGS. 2-11 (e.g., the Cu electrode or the microneedles that replace the LM nerve fibers 316). The EC-EYE 1202 may be configured to capture and/or acquire images and provide this information to the computing device 1206 via the electrical circuitry 1204. For instance, each of the LM nerve fibers may be electrically coupled to a plurality of NW from the NW array retina. The NW may acquire information and then provide the information to the electrical circuitry 1204.

In some examples, the EC-EYE 1202 may include single and/or multiple NW based EC detectors. The EC-EYE 1202 may use the single and/or multiple NW based EC detectors for acquiring/capturing images.

In some variations, the EC-EYE 1202 may include microneedles (e.g., Ni microneedles). The EC-EYE 1202 may use the microneedles for acquiring/capturing images.

The EC-EYE 1202 is electrically coupled to the electrical circuitry 1204. In some instances, the electrical circuitry 1204 may be a wired connection to the computing device 1206. In other instances, the electrical circuitry 1204 may include a multiplexer, current meter, power source, ground, and/or additional circuitry components. The electrical circuitry 1204 electrically couples the EC-EYE 1202 to the computing device 1206.

The computing device 1206 may be and/or include, but is not limited to, a desktop, laptop, an internet of things (IOT)

device, or any other type of computing device that generally comprises one or more communication components, one or more processing components, and/or one or more memory components. In some variations, the computing device 1206 may be implemented as engines, software functions, and/or applications. In other words, the functionalities of the computing device 1206 may be implemented as software instructions stored in storage (e.g., memory) and executed by one or more processors.

The computing device 1206 may receive the information from the EC-EYE 1202 via the electrical circuitry 1204. Using the information, the computing device 1206 may generate an image and then cause display of the image on the display device 1208. The computing device 1206 may further provide information to the electrical circuitry 1204 such as providing instructions for controlling a multiplexer of the electrical circuitry 1204.

In some examples, the computing device 1206 includes a processor, such as a central processing unit (CPU), controller, and/or logic, that executes computer executable instructions for performing the functions, processes, and/or methods described herein. In some instances, the computer executable instructions are locally stored and accessed from a non-transitory computer readable medium.

Figure 13:
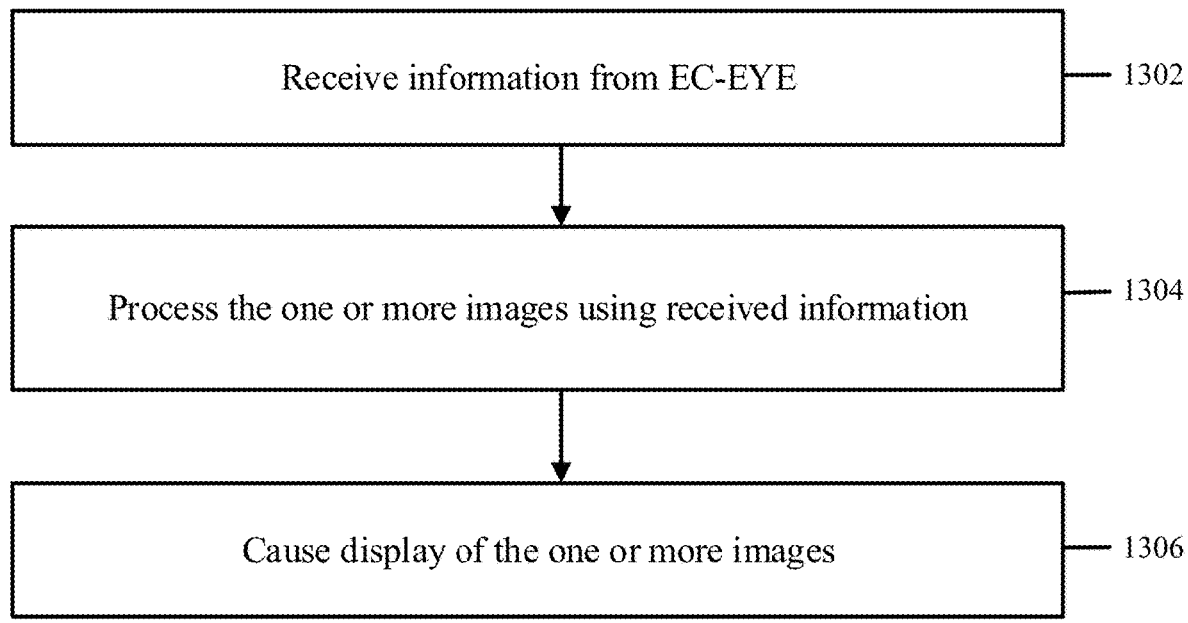
FIG. 13 shows an exemplary process for using the EC-EYE to capture images.

FIG. 13 shows an exemplary process 1300 for using the EC-EYE to capture images. The process 1300 may be performed by any type of system that includes an EC-EYE and a computing device such as system 1000 and/or system 1200.

At block 1302, the computing device may receive information from the EC-EYE (e.g., EC-EYE 1202 and/or 300). For example, as mentioned previously, the EC-EYE may include a NW device (e.g., the NW array 314, a hemispherical PAM, and/or a planar PAM) and a connection device (e.g., the Cu electrode, the LM nerve fibers 316, and/or the microneedles). The NW device may comprise a plurality of NWs that are configured to generate currents based on a detected light intensity. For instance, the generated current value may be associated with how much light is detected by the NWs. Further, a subset of NWs may be associated with a particular pixel within an image. After generating the current, the NWs provide the generated current to the computing device via the connection device. For instance, the connection device may be the LM nerve fibers 316 and each LM nerve fiber may connect a subset of NWs to the computing device. A photodetector, in such instances, may comprise, among other components, the single LM nerve fiber as well as its subset of NWs and each photodetector may be associated with a different pixel within an image. In some instances, the connection device may comprise a plurality of connectors. For instance, the connection device may comprise a plurality of LM nerve fibers 316 and each of the LM nerve fibers may be a connector. Additionally, and/or alternatively, the connection device may comprise a plurality of microneedles and each microneedle may be a connector.

At block 1304, the computing device may process the images. For instance, the computing device may determine pixel characteristics (e.g., luminance values, RGB values, and/or other values) for pixels within an image. Then, the computing device may generate the image using the pixel characteristics. For instance, each photodetector may be assigned to a particular pixel within and the current generated from the corresponding NWs may be used to determine the pixel characteristic for the pixel. The computing device may determine the pixel characteristic for a pixel using the current as well as what photodetector generated the current.

In some instances, a multiplexer may be used to connect the connection device to the computing device. The multiplexer may have channel information and the channel information may be used to determine the pixel characteristic for a particular pixel. For instance, a first channel of the multiplexer may be assigned to a pixel on the top right corner of the image. The NWs of a particular photodetector may generate the current and the connection device inputs the current to the first channel of the multiplexer. The computing device may receive information indicating the generated current and the channel information indicating that this current was received using the first channel of the multiplexer, which is associated with the particular photodetector. The computing device may determine the pixel characteristic using the current and the location of the pixel within the image (e.g., top right corner) using the channel information.

At block 1306, the computing device may cause display of the images on a display device. For instance, the computing device may provide the image to the display device and the display device may display the image.

In some variations, the spherical EC-EYE (e.g., the EC-EYE 300) may be fabricated as follows. The fabrication process may start by deforming a thick (500 μm) Al sheet on a set of hemispherical molds to manufacture a hemispherical Al shell (e.g., the Al shell 306). The hemispherical Al shell (e.g., the Al shell 306) may then undergo a standard two-step anodization process to form PAM with 40 μm thickness and nano-channel pitch and diameter of 500 nm and 120 nm, respectively, on Al surface. A barrier thinning process and Pb electrodeposition may be carried out to obtain Pb nanoclusters at the bottom of PAM channels. Afterwards, the outer layer of PAM and the residual Al may be etched away to obtain a freestanding PAM with Pb, which may then be transferred into a tubular furnace for ~5 μm long perovskite NW growth (e.g., for the NW array 314). A 20 nm thick Indium layer (e.g., the Indium adhesion layer 310) may be then prepared by evaporating it onto the PAM back surface to serve as adhesion layer. This Indium layer might not cause short circuit between pixels due to its discontinuous morphology. To obtain LM contact array (e.g., the LM fibers 316), a hedgehog shaped mold may be fabricated using 3-D printing, from which a complementary PDMS socket (e.g., the PDMS eye socket 312) with 10×10 hole array (hole size: 700 μm, pitch: 1.6 mm) may be casted. EGaIn LM may then be injected into thin soft tubes (inner diameter: 400 μm, outer diameter: 700 μm) to form LM wires (e.g., the LM fibers 316). Then, 100 tubes may be inserted into the holes on the PDMS socket (e.g., the PDMS socket 312) and the whole socket may be attached to the PAM/NW surface to form 10×10 photodetector array (e.g., the LM nerve fibers 316). These long soft tubes may be directly connected to printed circuit board (PCB) and thus the complex wire bonding process may be avoided. A circular hole may be opened on another Al shell, which may then be coated with a tungsten film (e.g., the W film contact 306) working as counter electrode of EC-EYE. After mounting the aperture (e.g., the aperture 304), the Al shell may be subsequently fixed onto front side of PAM by epoxy. Ionic liquid (e.g., the ionic liquid 308) 1-Butyl-3-methylimidazolium bis(trifluoromethylsulfonyl)imide (BMIMTFSI) mixed with 1 v % of 1-Butyl-3-methylimidazolium iodide (BMIMI) may then be injected and a lens (e.g., the lens 302) may then be glued to the hole on Al shell to seal the device. After curing, the EC-EYE device 300 fabrication is completed.

Figure 14:
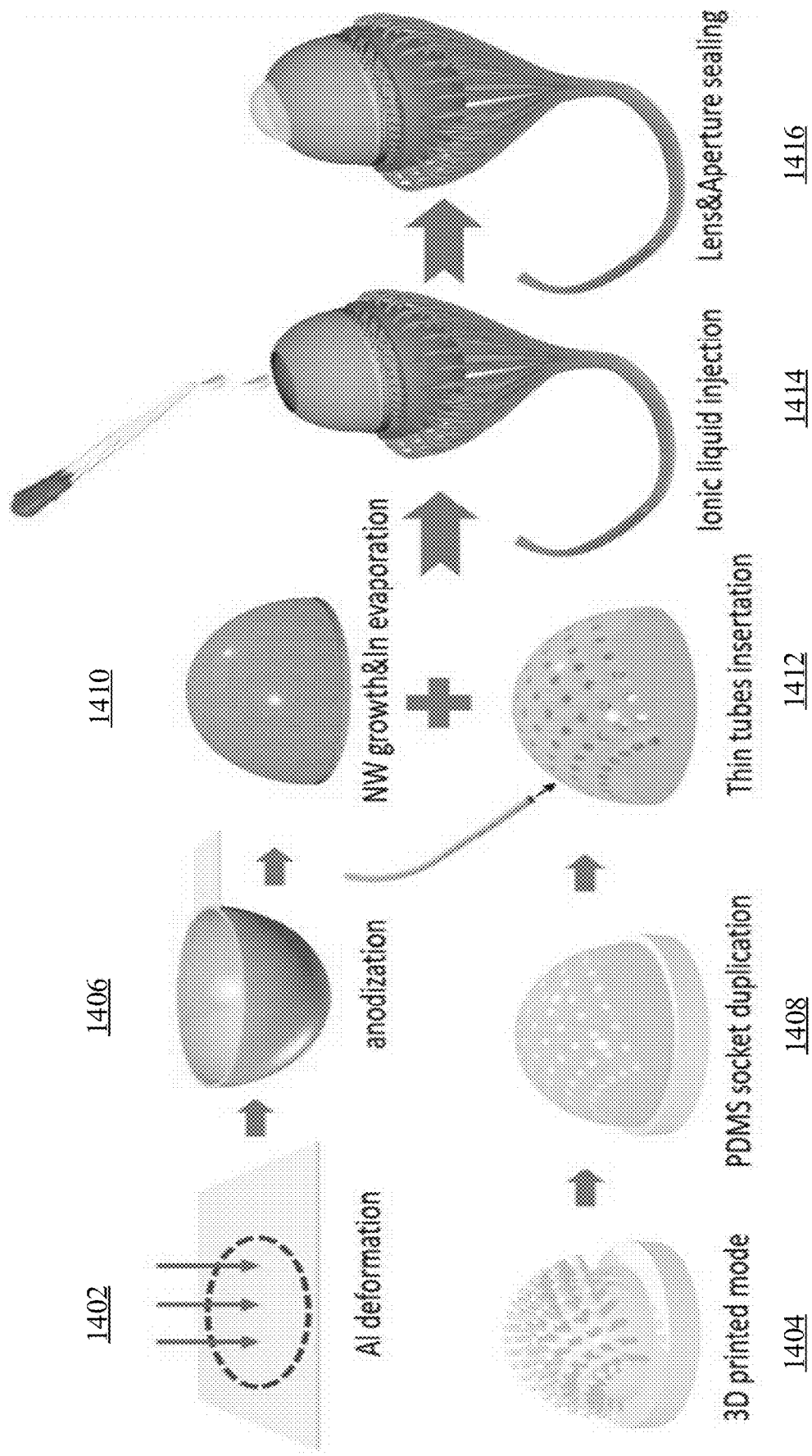
FIG. 14 shows a schematic fabrication process of an EC-EYE.

FIG. 14 shows a schematic fabrication process 1400 of an EC-EYE (e.g., EC-EYE 300). For instance, at stage 1402, Al deformation is performed. At stage 1404, 3-D printed mode is used to print the NWs. At stage 1406, an anodization process is performed. At stage 1408, the PDMS socket duplication is performed. At stage 1410, the NW growth and In evaporation is performed. At stage 1412, the thin tubes insertion is performed. Based on stages 1410 and 1412, the ionic liquid injection is performed at stage 1414. Then, the lens and aperture sealing is performed at stage 1416.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system, comprising:
a biomimetic electrochemical eye (EC-EYE), comprising:
an ionic liquid device comprising ionic liquid that serves as an electrolyte to a plurality of nanowires (NWs);
a nanowire (NW) device that comprises the plurality of NWs configured to generate a plurality of currents based on a detected light intensity; and
a connection device operatively coupled to the NW device, wherein the connection device is configured to provide the plurality of currents associated with the plurality of NWs to a computing device; and
the computing device, wherein the computing device comprises:
one or more processors configured to:
receive the plurality of currents from the plurality of NWs via the connection device;
determine a plurality of pixel characteristics associated with a plurality of pixels based on the plurality of currents from the plurality of NWs;
generate an image comprising the plurality of pixels based on the plurality of pixel characteristics; and
provide the image to a display device; and
the display device, wherein the display device is configured to display the image.

2. The system of claim 1, wherein the connection device comprises a plurality of connectors, and wherein the one or more processors are configured to determine the plurality of pixel characteristics by:
determining a pixel characteristic for each pixel of the plurality of pixels based on currents generated by a subset of NWs of the plurality of NWs, wherein each of the subset of NWs is associated with a connector, of the plurality of connectors, that connects the subset of NWs to the computing device and is assigned to a single pixel from the plurality of pixels, and wherein the currents from the subset of NWs are used to determine the pixel characteristic for that single pixel.

3. The system of claim 2, wherein the pixel characteristic is a luminance value or a red, green, blue (RGB) value, and wherein the one or more processors are configured to determine the pixel characteristic for each pixel by:
determining the luminance value or the RGB value based on a value of the currents generated by the corresponding subset of NWs, wherein the value of the currents is based on the detected light intensity.

4. The system of claim 2, wherein the one or more processors are configured to determine the pixel characteristic for each pixel based on a summation of the currents generated by the subset of NWs that are assigned to the pixel.

5. The system of claim 1, wherein the EC-EYE further comprises:
a tungsten film contact configured to operate as a counter electrode to the plurality of NWs.

6. The system of claim 5, wherein the connection device comprises a plurality of liquid metal (LM) nerve fibers, wherein each of the connectors is an LM nerve fiber from the plurality of LM nerve fibers.

7. The system of claim 6, wherein the EC-EYE further comprises:
a polydimethylsiloxane (PDMS) eye socket configured to integrate and align the plurality of LM nerve fibers with the plurality of NWs; and
an indium adhesion layer configured to be an electrical contact between the plurality of NWs and the plurality of LM nerve fibers,
wherein the NW device is a NW array retina that is hemispherical in shape and the EC-EYE is spherical in shape.

8. The system of claim 6, further comprising:
a multiplexer, wherein each of the plurality of LM nerve fibers is an input to the multiplexer and an output of the multiplexer is provided to the computing device, wherein each of the inputs of the multiplexer is associated with a pixel from the plurality of pixels.

9. The system of claim 1, wherein the NW device is a hemispherical porous-alumina-membrane (PAM) and the plurality of NWs are grown inside the hemispherical PAM using a vapor-phase process.

10. The system of claim 9, wherein the plurality of NWs comprise a metal-halide perovskite material, a silicon (Si) material, a germanium (Ge) material, an indium phosphide (InP) material, or a gallium arsenide (GaAs) material.

11. The system of claim 1, wherein the NW device is a planar porous-alumina-membrane (PAM), wherein the connection device is a Copper (Cu) electrode that is operatively coupled to the plurality of NWs, and wherein the Cu electrode is configured to provide the plurality of currents generated by the plurality of NWs to the computing device.

12. The system of claim 11, wherein the planar PAM is fabricated using a two-step anodization process followed by mercury (II) chloride ($HgCl_2$) etching, wherein the plurality of NWs are a plurality of perovskite NWs, and wherein the plurality of perovskite NWs are grown within a plurality of channels within the planar PAM.

13. The system of claim 1, wherein the connection device comprises a plurality of microneedles that are configured to provide the plurality of currents generated by the plurality of NWs to the computing device, wherein each microneedle is associated with a subset of NWs of the plurality of NWs and configured to provide only the current generated from the subset of NWs to the computing device.

14. The system of claim 13, wherein the plurality of microneedles are a plurality of nickel (Ni) microneedles, wherein each subset of NWs comprises three NWs, and wherein each microneedle is configured to provide the current generated by the three corresponding NWs to the computing device.

15. The system of claim 13, further comprising:
a multiplexer, wherein each of the plurality of microneedles is an input to the multiplexer and an output of the multiplexer is provided to the computing device,
wherein the one or more processors are configured to determine the plurality of pixel characteristics based on:
determining a pixel characteristic, from the plurality of pixel characteristics, of a pixel based on a received current of the plurality of currents;
determining a corresponding input of the multiplexer that provided the received current; and
determining a location of the pixel within the image based on the corresponding input of the multiplexer.

16. A method, comprising:
receiving, by a computing device, a plurality of currents from a plurality of nanowires (NWs) of a biomimetic electrochemical eye (EC-EYE), wherein the EC-EYE comprises the plurality of NWs, an ionic liquid device, and a connection device, wherein the ionic liquid device comprises ionic liquid that serves as an electrolyte to the plurality of NWs, wherein the plurality of NWs are configured to generate a plurality of currents based on a detected light intensity, and wherein the connection device is operatively coupled to the NW device and configured to provide the plurality of currents associated with the plurality of NWs to the computing device;
determining, by the computing device, a plurality of pixel characteristics associated with a plurality of pixels based on the plurality of currents from the NWs;
generating, by the computing device, an image comprising the plurality of pixels based on the plurality of pixel characteristics; and
causing, by the computing device, display of the image on a display device.

17. The method of claim 16, wherein the connection device comprises a plurality of connectors, and wherein determining the plurality of pixel characteristics comprises:
determining a pixel characteristic for each pixel of the plurality of pixels based on currents generated by a subset of NWs of the plurality of NWs, wherein each subset of NWs is associated with a connector, of the plurality of connectors, that connects the subset of NWs to the computing device and is assigned to a single pixel from the plurality of pixels, and wherein the currents from the subset of NWs are used to determine the pixel characteristic for that single pixel.

18. The method of claim 17, wherein the pixel characteristic is a luminance value or a red, green, blue (RGB) value, and wherein determining the pixel characteristic for each pixel comprises:
determining the luminance value or the RGB value based on a value of the current generated by the corresponding subset of NWs, wherein the value of the current is based on the detected light intensity.

19. A biomimetic electrochemical eye (EC-EYE), comprising:
a nanowire (NW) device that comprises a plurality of perovskite NWs, wherein each of the plurality of perovskite NWs is configured to generate a current based on a detected light intensity, and wherein the plurality of perovskite NWs are grown on the NW device using a vapor-phase process, wherein the NW device is hemispherical and the EC-EYE is spherical;
a plurality of liquid metal (LM) nerve fibers operatively coupled to the NW device, wherein the plurality of LM nerve fibers are configured to provide a plurality of currents associated with the plurality of perovskite NWs to a computing device, wherein each of the LM nerve fibers is electrically connected to a subset of the plurality of perovskite NWs; and
a polydimethylsiloxane (PDMS) eye socket with a hole array for the plurality of LM nerve fibers, wherein the PDMS nerve socket is fabricated using a 3-dimensional (3-D) printer, wherein the plurality of LM nerve fibers are injected into tubes using LM patterning and inserted into holes of the hole array.

20. The EC-EYE of claim 19, wherein the NW device is a hemispherical porous-alumina-membrane (PAM), and wherein the EC-EYE further comprises:
an indium adhesion layer that is operatively coupled to the hemispherical PAM, wherein the indium adhesion layer is evaporated onto a side of the PAM opposite the plurality of perovskite NWs;
a hemispherical aluminum (Al) shell that is coated with a tungsten film and configured to be a counter electrode for the EC-EYE; and
an ionic liquid humour that comprises an ionic liquid and positioned between the AL shell that is coated with the tungsten film and the PAM.

* * * * *